(12) United States Patent
Chang et al.

(10) Patent No.: US 11,078,582 B2
(45) Date of Patent: Aug. 3, 2021

(54) SUPRAMOLECULAR PORPHYRIN CAGES ASSEMBLED AT MOLECULAR-MATERIALS INTERFACES FOR ELECTROCATALYTIC CO REDUCTION

(71) Applicants: Christopher J Chang, Berkeley, CA (US); Ming Gong, San Pablo, CA (US); Zhi Cao, Albany, CA (US); Wei Liu, Oxford, OH (US)

(72) Inventors: Christopher J Chang, Berkeley, CA (US); Ming Gong, San Pablo, CA (US); Zhi Cao, Albany, CA (US); Wei Liu, Oxford, OH (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/116,822

(22) Filed: Aug. 29, 2018

(65) Prior Publication Data
US 2019/0062936 A1    Feb. 28, 2019

Related U.S. Application Data

(60) Provisional application No. 62/551,633, filed on Aug. 29, 2017.

(51) Int. Cl.
| | | |
|---|---|---|
| C07D 487/22 | (2006.01) | |
| C25B 11/075 | (2021.01) | |
| C07C 1/10 | (2006.01) | |
| C07C 29/159 | (2006.01) | |
| B01J 19/08 | (2006.01) | |
| C07C 51/10 | (2006.01) | |
| C07D 487/14 | (2006.01) | |
| C25B 3/25 | (2021.01) | |

(52) U.S. Cl.
CPC ......... C25B 11/075 (2021.01); B01J 19/088 (2013.01); C07C 1/10 (2013.01); C07C 29/159 (2013.01); C07C 51/10 (2013.01); C07D 487/14 (2013.01); C07D 487/22 (2013.01); C25B 3/25 (2021.01); B01J 2219/0892 (2013.01)

(58) Field of Classification Search
CPC .................................................. C07D 487/22
See application file for complete search history.

(56) References Cited

PUBLICATIONS

Collman et al. (JACS, 1982, 104, 5, 1391-1403).*
Tanaka et al. (Catalysis Today, 183, 2012, 108-118).*

* cited by examiner

Primary Examiner — Brian E McDowell
(74) Attorney, Agent, or Firm — Robin C. Chiang; Lawrence Berkeley National Laboratory

(57) ABSTRACT

The present invention provides for a composition comprising a heterostructure capable of electrochemical CO reduction to a carbon-carbon product, comprising an inorganic material and a porous molecule. In some embodiments, the heterostructure comprises the following structure:

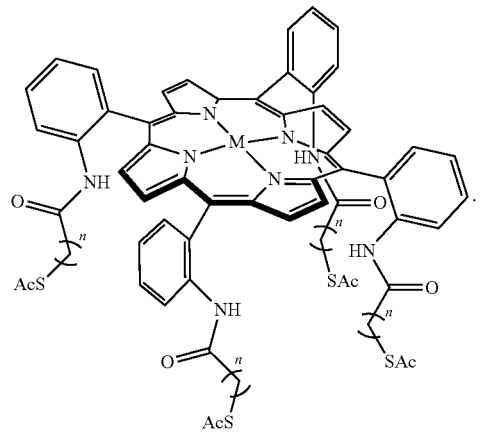

13 Claims, 22 Drawing Sheets

$$2\,CO + 3\,H_2O + 4\,e^- \longrightarrow CH_3COO^- + 3\,OH^- \quad \text{acetate}$$
$$2\,CO + 7\,H_2O + 8\,e^- \longrightarrow CH_3CH_2OH + 8\,OH^- \quad \text{ethanol}$$
$$2\,CO + 6\,H_2O + 8\,e^- \longrightarrow CH_2{=}CH_2 + 8\,OH^- \quad \text{ethylene}$$

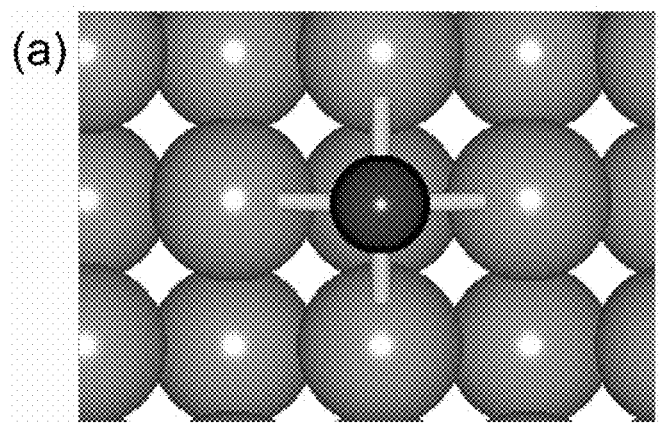
Figure 18A
Figure 18B
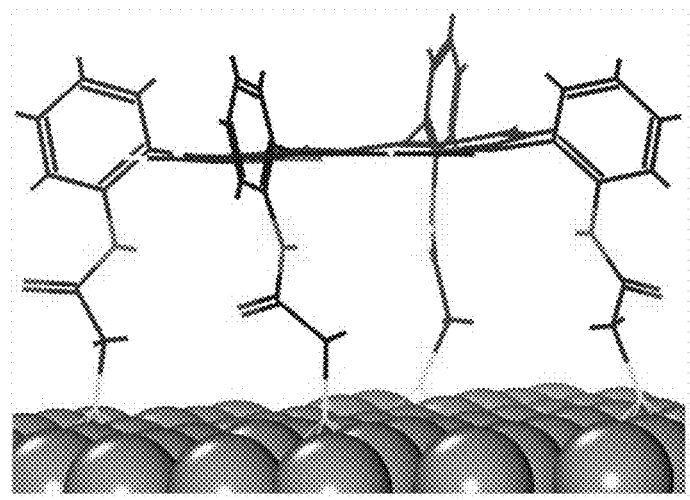
Figure 19

SUPRAMOLECULAR PORPHYRIN CAGES ASSEMBLED AT MOLECULAR-MATERIALS INTERFACES FOR ELECTROCATALYTIC CO REDUCTION

CROSS REFERENCE TO RELATED APPLICATIONS

This application claims priority to U.S. Provisional Patent Application Ser. No. 62/551,633, filed Aug. 29, 2017.

STATEMENT OF GOVERNMENTAL SUPPORT

The invention described and claimed herein was made in part utilizing funds supplied by the U.S. Department of Energy under Contract No. DE-AC02-05CH11231 between the U.S. Department of Energy and The Regents of the University of California for the management and operation of the Lawrence Berkeley National Laboratory. The government has certain rights in this invention.

BACKGROUND OF THE INVENTION

Field of the Invention

The present invention relates to the field of carbon monoxide (CO) reduction and supramolecular cages at molecular-materials interfaces.

Related Art

Climate change and rising global energy demands motivate broad interest in carbon fixation to value-added products with formation of carbon-carbon bonds.[1-6] In this context, carbon monoxide (CO) is a common one-carbon product of carbon dioxide ($CO_2$) reduction[7-27] and major feedstock for producing multicarbon products as illustrated by the classic Fischer-Tropsch process.[28,29] Electrochemical CO reduction offers a complementary approach to C—C coupling reactivity with sustainable energy input,[30-33] where reducing hydrogen equivalents can be provided directly by aqueous electrolytes and thus bypass the traditionally energy-intensive steam reforming process for $H_2$ production. Reports of electrochemical CO reduction are exceedingly rare relative to $CO_2$ reduction and have focused largely on copper, which can reduce CO to C2 products including ethanol, acetate, and ethylene; however, conventional Cu electrodes show poor selectivity for CO over proton reduction and low energetic efficiency.[33] Elegant work by Kanan et al. has utilized grain boundaries to improve CO over $H^+$ selectivity on heterobimetallic cavities (e.g., NiFe or MoCu) with pendant electron reservoirs.

BRIEF DESCRIPTION OF THE INVENTION

The present invention provides for a composition comprising a heterostructure capable of electrochemical CO reduction to a carbon-carbon product, comprising an inorganic material and a porous molecule.

In some embodiments, the inorganic material is 2H, any metal, or halide thereof, or any compound described in Table 1 herein. In some embodiments, the porous molecule is an organic molecule, such as a porphyrin.

In some embodiments, the heterostructure comprises the following structure:

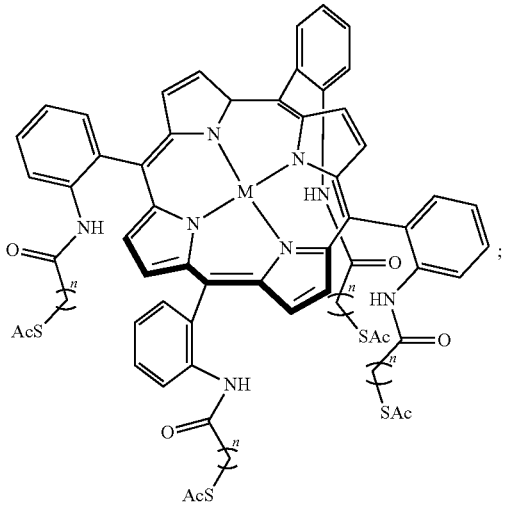

wherein (a) M is 2H or any metal, or halide thereof, or any inorganic material described in Table 1, and (b) n is any integer from (0 or 1) to 20.

In some embodiments, M is any transition metal. In some embodiments, M is Sc, Ti, V. Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Rf, Db, Sg, Bh, or Hs, or a halide thereof. In some embodiments, the halide is a fluoride, bromide or chloride.

In some embodiments, n is any integer from 0 (or 1) to 10. In some embodiments, n is 1, 2, 3, 4, 5, 6, 7, 8, or 9.

In some embodiments, the heterostructure is capable of electrochemical CO reduction to a carbon-carbon product with one or more of the following properties: a Faradaic efficiency equal to or greater than 40%, a current density of equal to greater than 1.34 $mA/cm^2$), and a potential of −0.40 V vs RHE. In some embodiments, the heterostructure is capable of electrochemical CO reduction to a carbon-carbon product with a Faradaic efficiency equal to or greater than 40%, 50%, 60%, 60%, 70%, or 80%, or any value described herein. In some embodiments, the heterostructure is capable of electrochemical CO reduction to a carbon-carbon product with a current density of equal to greater than 0.5, 0.6, 0.7, 0.8, 0.9, 1.0, 1.1, 1.2, or 1.3 $mA/cm^2$, or any value described herein.

The present invention also provides for any method or composition described herein.

BRIEF DESCRIPTION OF THE DRAWINGS

The foregoing aspects and others will be readily appreciated by the skilled artisan from the following description of illustrative embodiments when read in conjunction with the accompanying drawings.

C., 20 h; (iv) n=1: bromoacetyl bromide; n=2: 3-bromopropionyl bromide; n=3: 4-chlorobutyryl chloride; n=4: 5-chlorovaleroyl chloride; (v) KSAc, THF, 4 h; (vi) $MCl_2$ (M=Fe, Zn, and Ni), 2,6-lutidine, THF; B. Structures of porphyrins used in this study.

Figure 2A:
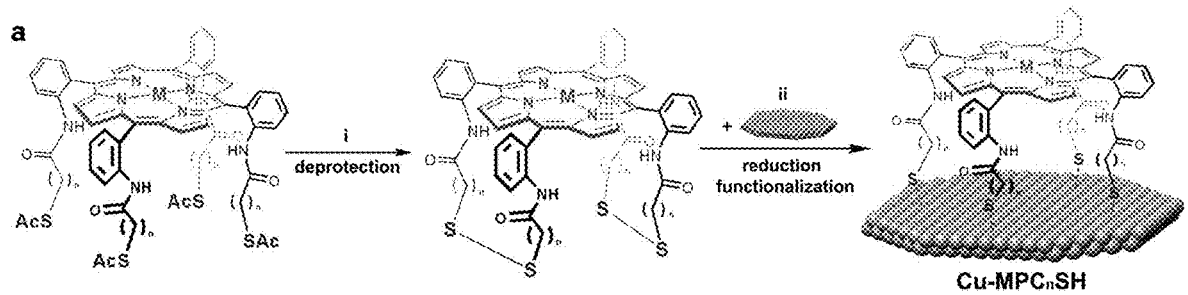

FIG. 2A shows the functionalization of Cu surfaces with porphyrin cages. (i) $NH_3$ in methanol/chloroform, 25° C., 4 h, (ii) sodium borohydride, DMF, 25° C., 12 h.

Figure 2B:
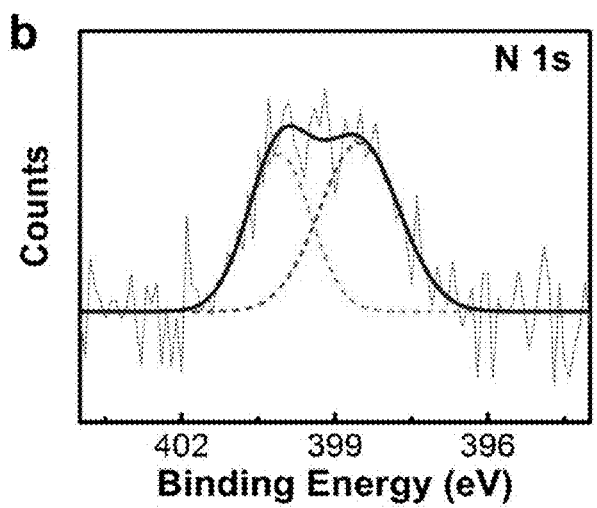

FIG. 2B shows high resolution N 1 s. The scan rate is 10 mV/s.

Figure 2C:
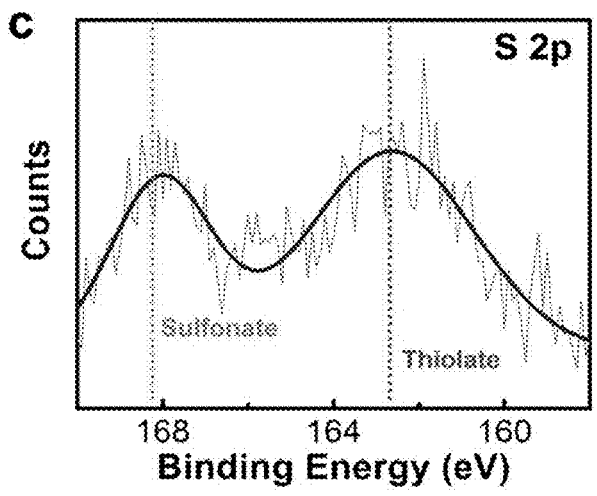

FIG. 2C shows S 2p XPS spectra of 100 nm Cu on Si wafer functionalized with porphyrin cages. The scan rate is 10 mV/s.

Figure 2D:
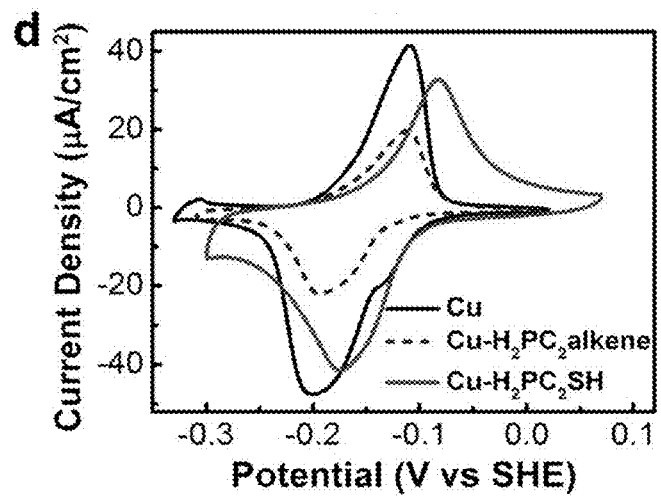

FIG. 2D shows cyclic voltammetry curves of underpotential deposition of Pb on Cu (black), Cu tethered with alkene-terminated porphyrins (dashed blue), Cu tethered with thiol-terminated porphyrins (red). The scan rate is 10 mV/s.

Figure 3A:
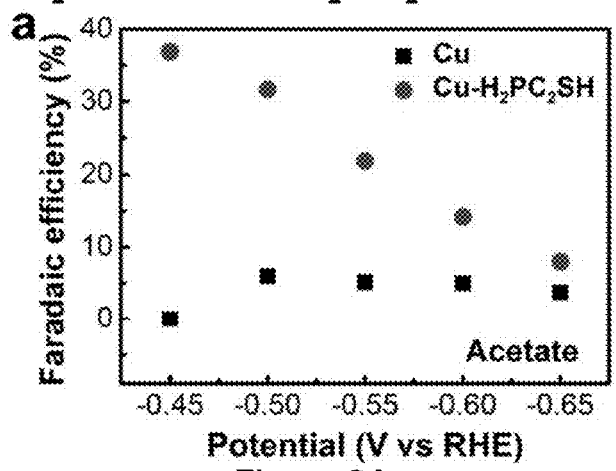

FIG. 3A shows faradaic efficiencies of CO reduction into acetate under different potentials on Cu foil and Cu—$H_2PC_2SH$ in CO-saturated 0.1 M KOH (aq). The electrolysis was performed at a constant potential of –0.55 V vs RHE.

Figure 3B:
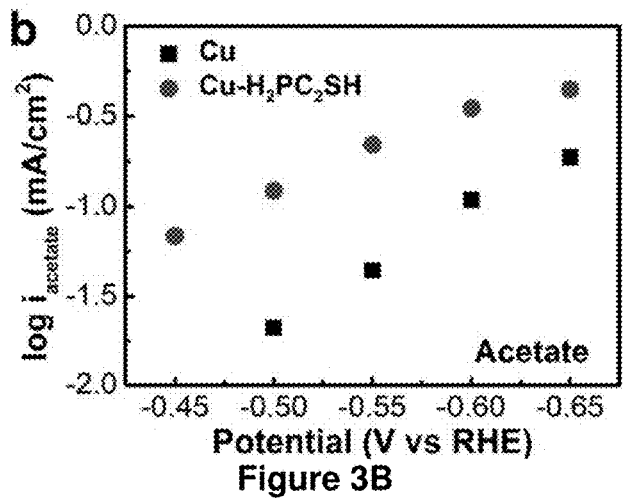

FIG. 3B shows specific current densities of CO reduction into acetate under different potentials on Cu foil and Cu—$H_2PC_2SH$ in CO-saturated 0.1 M KOH (aq). The electrolyses was performed at a constant potential of –0.55 V vs RHE.

Figure 3C:
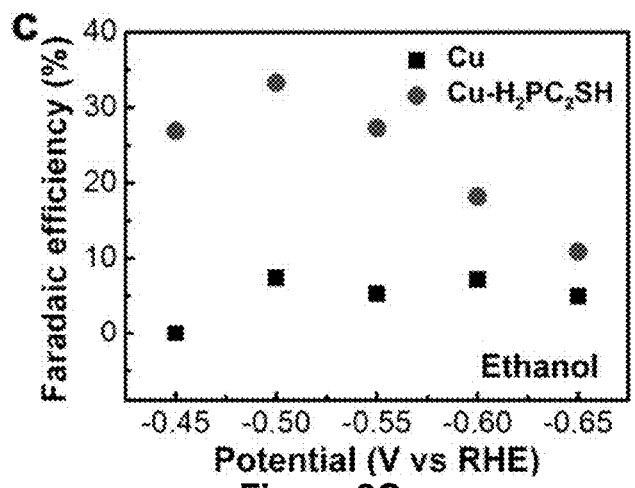

FIG. 3C shows faradaic efficiencies of CO reduction into ethanol under different potentials on Cu foil and Cu—$H_2PC_2SH$ in CO-saturated 0.1 M KOH (aq). The electrolyses was performed at a constant potential of –0.55 V vs RHE.

Figure 3D:
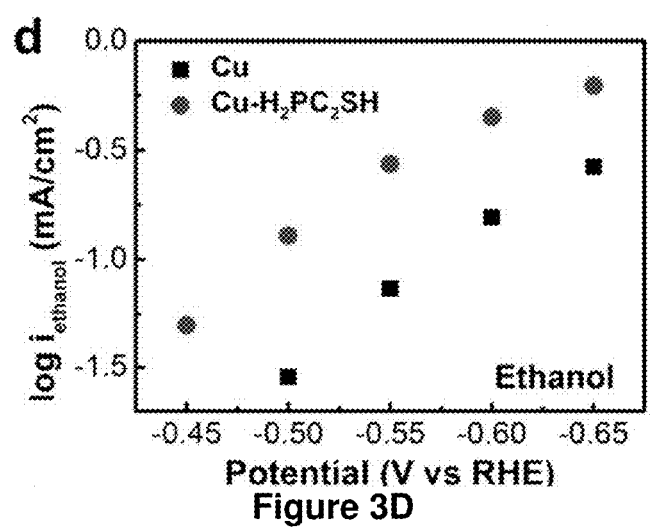

FIG. 3D shows specific current densities of CO reduction into ethanol under different potentials on Cu foil and Cu—$H_2PC_2SH$ in CO-saturated 0.1 M KOH (aq). The electrolyses was performed at a constant potential of –0.55 V vs RHE.

Figure 3E:
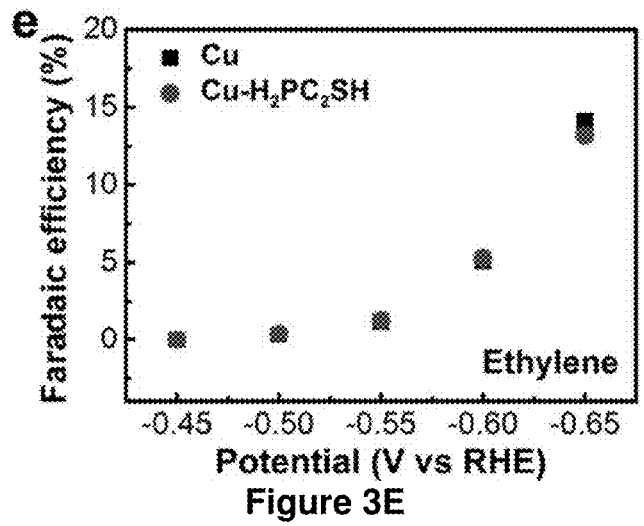

FIG. 3E shows faradaic efficiencies of CO reduction into ethylene under different potentials on Cu foil and Cu—$H_2PC_2SH$ in CO-saturated 0.1 M KOH (aq). The electrolyses was performed at a constant potential of –0.55 V vs RHE.

Figure 3F:
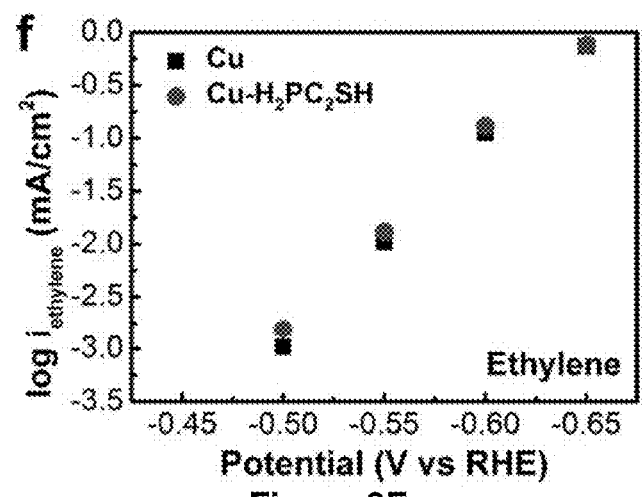

FIG. 3F shows specific current densities of CO reduction into ethylene under different potentials on Cu foil and Cu—$H_2PC_2SH$ in CO-saturated 0.1 M KOH (aq). The electrolyses was performed at a constant potential of –0.55 V vs RHE.

Figure 4A:
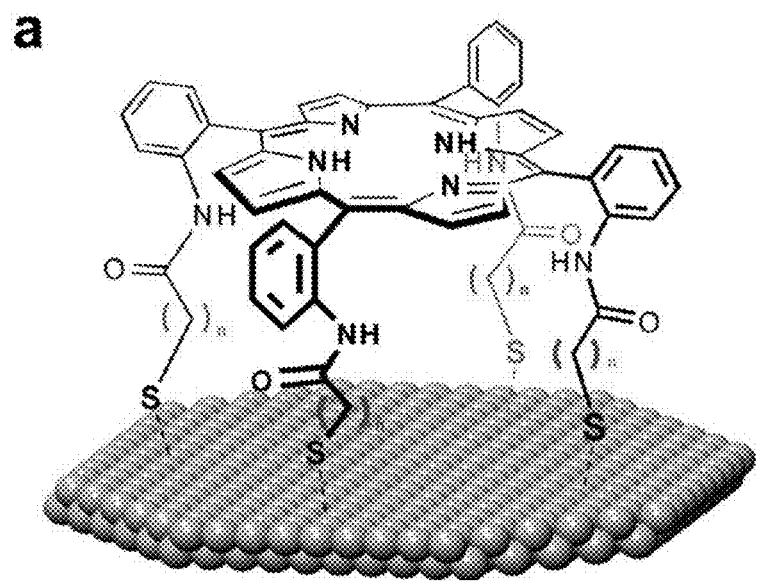

FIG. 4A shows free-base porphyrins possessing different linker lengths.

Figure 4B:
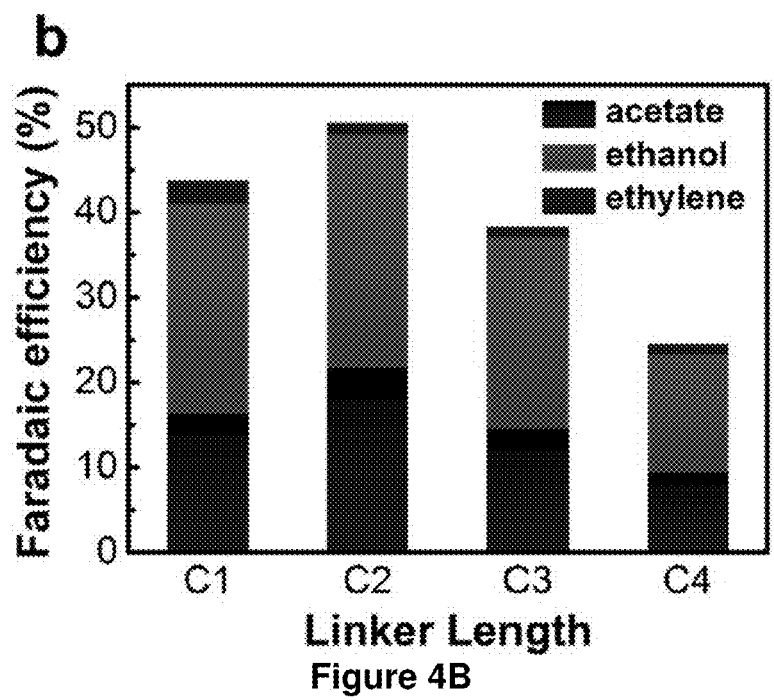

FIG. 4B shows Faradaic efficiencies for CO reduction on Cu foils functionalized with free-base porphyrins possessing different linker lengths (Cu—$H_2PC_nSH$). The electrolyses were performed at a constant potential of –0.55 V vs RHE in CO-saturated 0.1 M KOH (aq).

Figure 5A:
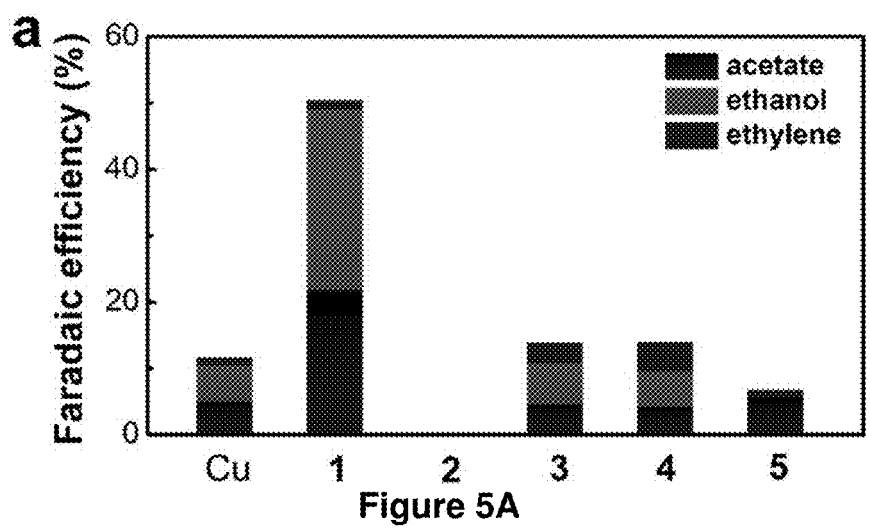

FIG. 5A shows specific Faradaic efficiencies of CO reduction on Cu—$H_2PC_2SH$ in comparison with Cu foil and other control groups. 1. Cu+$H_2PC_2SH$, 2. Cu+$C_{12}SH$, 3. Cu+3-MMPA, 4. Cu+$H_2PAA$, 5. Cu+$H_2$-p-$PC_2SH$. The electrolysis was performed at a constant potential of –0.55 V vs RHE in CO-saturated 0.1 M KOH (aq).

Figure 5B:
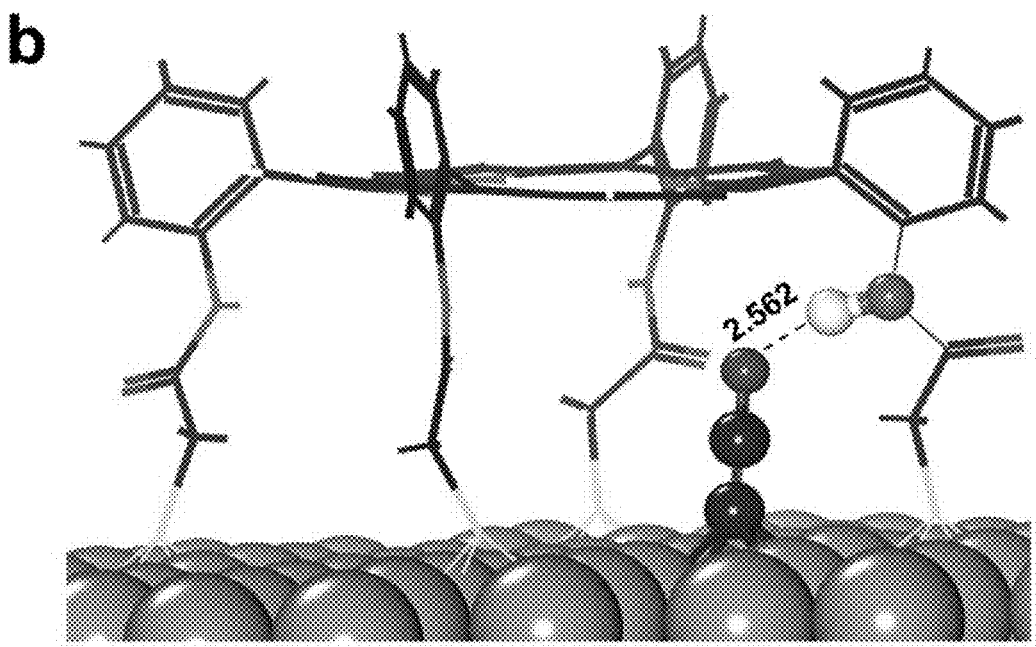

FIG. 5B shows DFT calculation of a speculative ketene intermediate within the porphyrin cage formed on Cu(100) surfaces, which identifies a potential rationalization for differences in CO reduction selectivity for different cage sizes but does not rule out other plausible mechanistic possibilities.

Figure 6A:
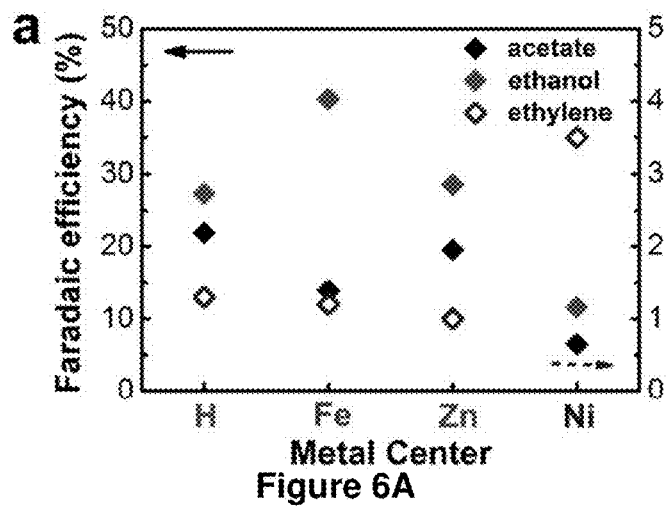

FIG. 6A shows Faradaic efficiencies for CO reduction on Cu foils functionalized with metalloporphyrins containing different metal centers (Cu-MPC$_2$SH). The electrolysis was performed at a constant potential of –0.55 V vs RHE in CO-saturated 0.1 M KOH (aq).

Figure 6B:
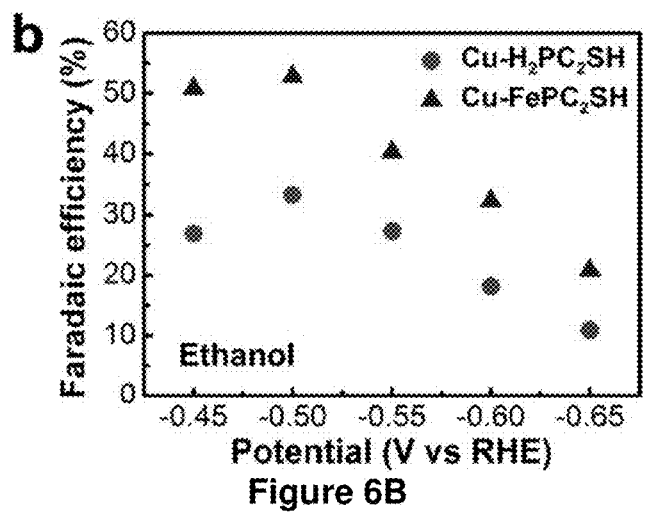

FIG. 6B shows Faradaic efficiencies and current densities for CO reduction into ethanol under different potentials with Cu—$H_2PC_2SH$ and Cu—$FePC_2SH$ in CO-saturated 0.1 M KOH (aq).

Figure 6C:
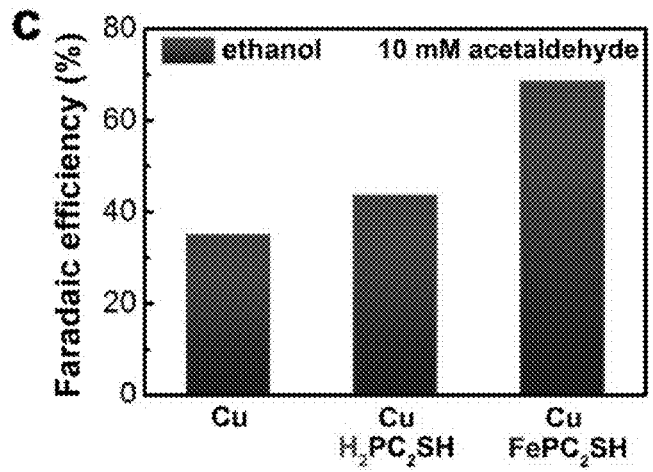

FIG. 6C shows Faradaic efficiencies of acetaldehyde reduction into ethanol on Cu foil, Cu—$H_2PC_2SH$ and Cu—$FePC_2SH$ in Ar-saturated 0.1 M KOH (aq) with 10 mM acetaldehyde at a constant potential of –0.40 V vs RHE.

Figure 6D:
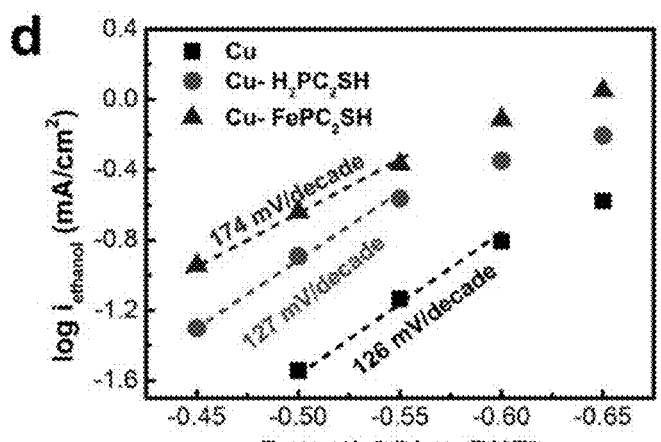

FIG. 6D shows Tafel plots of specific current densities of CO reduction into ethanol on Cu, Cu—$H_2PC_2SH$ and Cu—$FePC_2SH$ in CO-saturated 0.1 M KOH (aq).

Figure 6E:
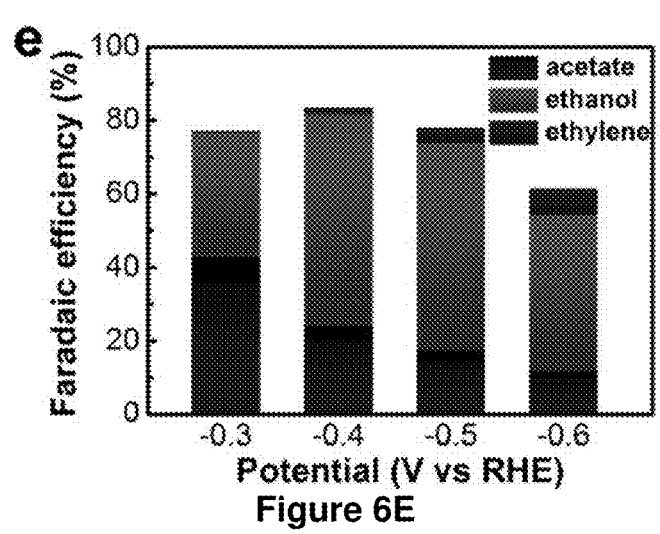

FIG. 6E shows specific Faradaic efficiencies CO reduction on electrodeposited Cu functionalized with iron porphyrins ($FePC_2SH$).

Figure 6F:
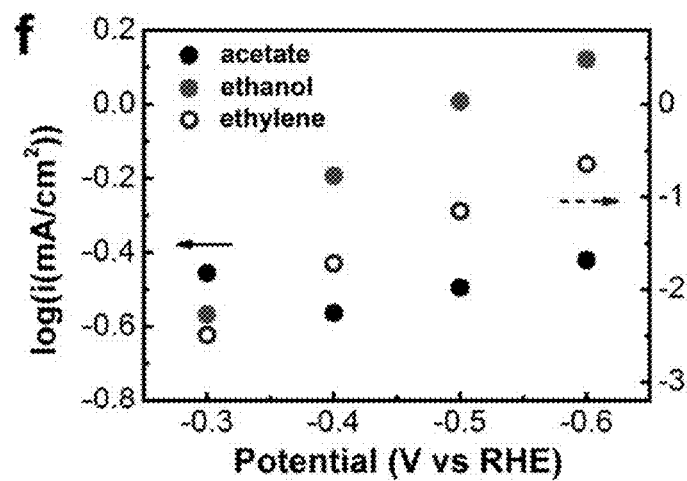

FIG. 6F shows specific current densities of CO reduction on electrodeposited Cu functionalized with iron porphyrins ($FePC_2SH$). The ethylene current density corresponds to the right y-axis.

Figure 7A:
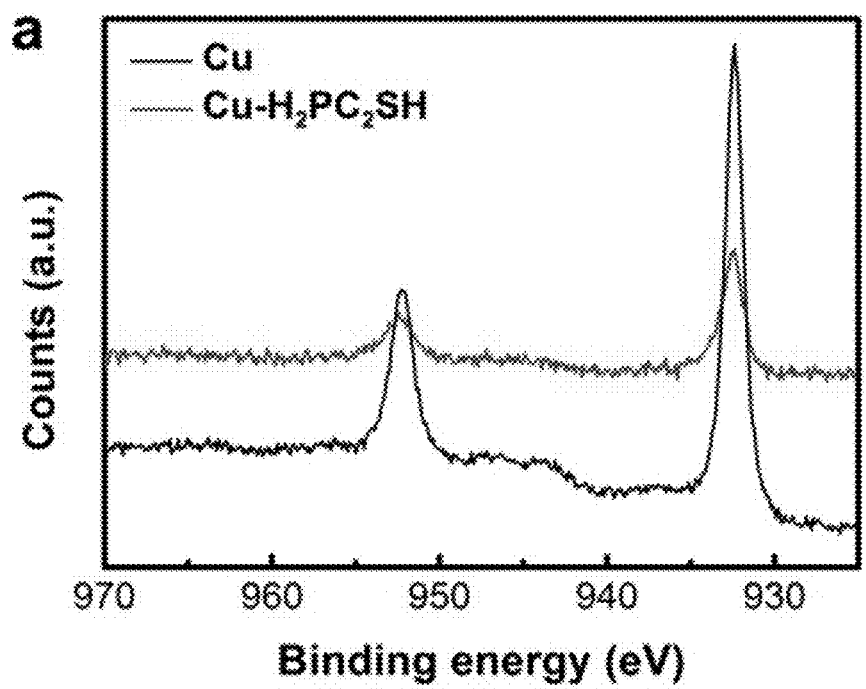

FIG. 7A shows a high resolution Cu 2p XPS spectra of 100 nm Cu on Si with and without $H_2PC_2SH$ functionalization.

Figure 7B:
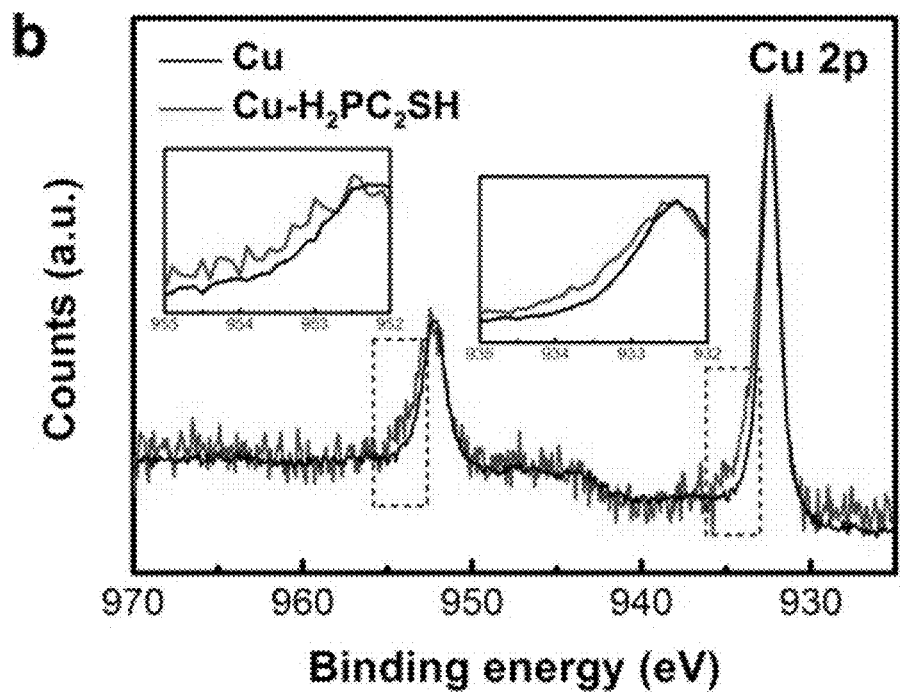

FIG. 7B shows a comparison of spectra with normalized peak counts showing the presence of extended tail features at higher energies for porphyrin-functioned Cu relative to control.

Figure 8:
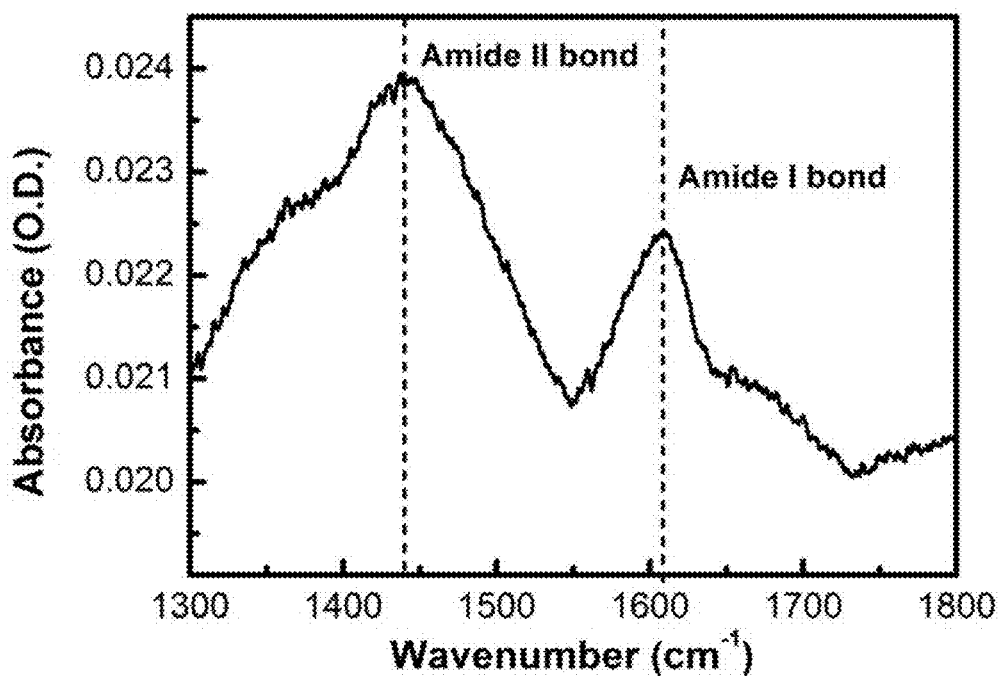

FIG. 8 shows an external reflection FTIR spectrum of the Cu—$FePC_2SH$ (on 100 nm Cu/Si) showing observable amide-bond bands.

Figure 9:
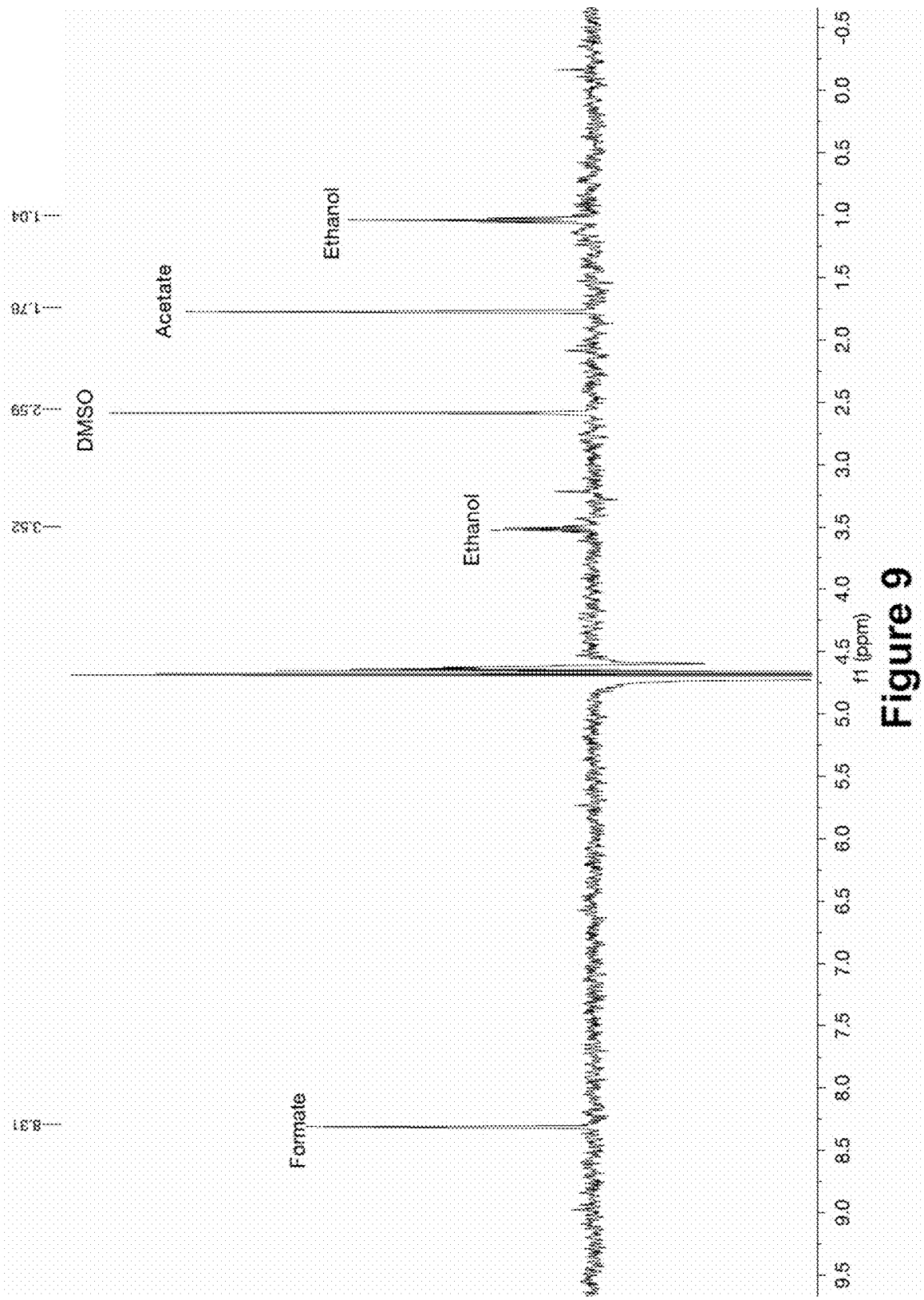

FIG. 9 shows representative NMR spectrum for bulk electrolysis with $H_2PC_2SH$-capped Cu foil at –0.6 vs RHE in 0.1 M KOH saturated with CO. Formate was generated by chemical reaction of CO and $OH^−$ without any electron transfer.

Figure 10A:
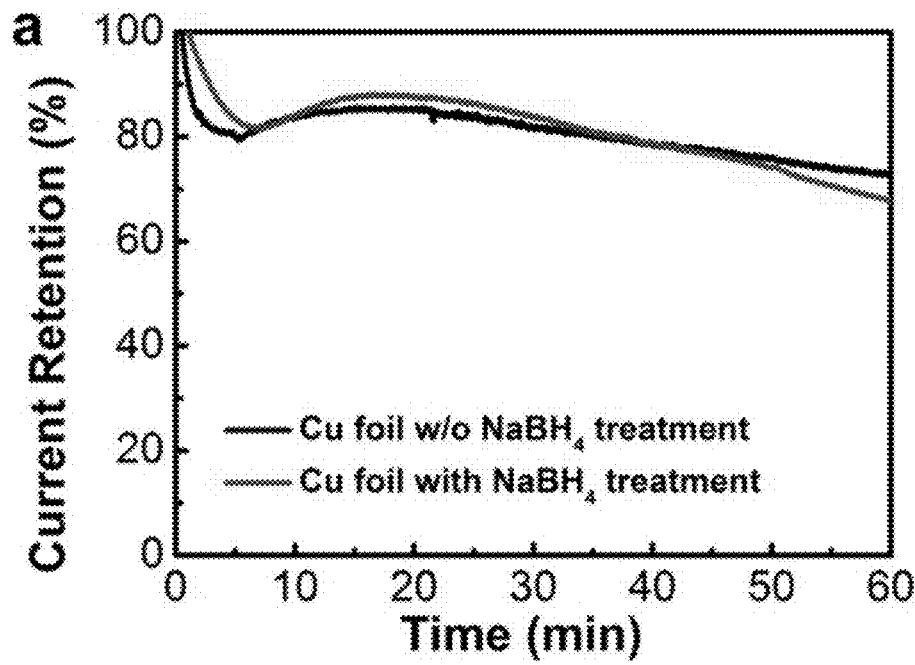

FIG. 10A shows controlled potential electrolysis curves of control Cu foils with and without $NaBH_4$ treatment (the identical porphyrin functionalization procedure but without porphyrin addition) at a potential of –0.55 V vs RHE in 0.1 M KOH saturated with CO.

Figure 10B:
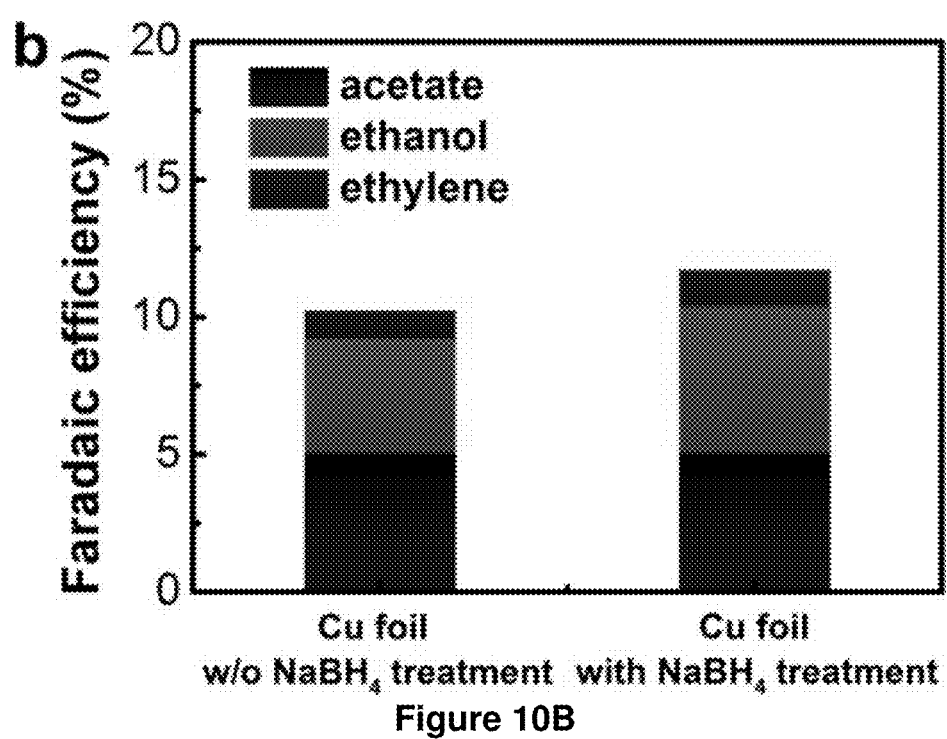

FIG. 10B shows Faradaic efficiencies for CO reduction on control Cu foils with and without borohydride treatment.

Figure 11:
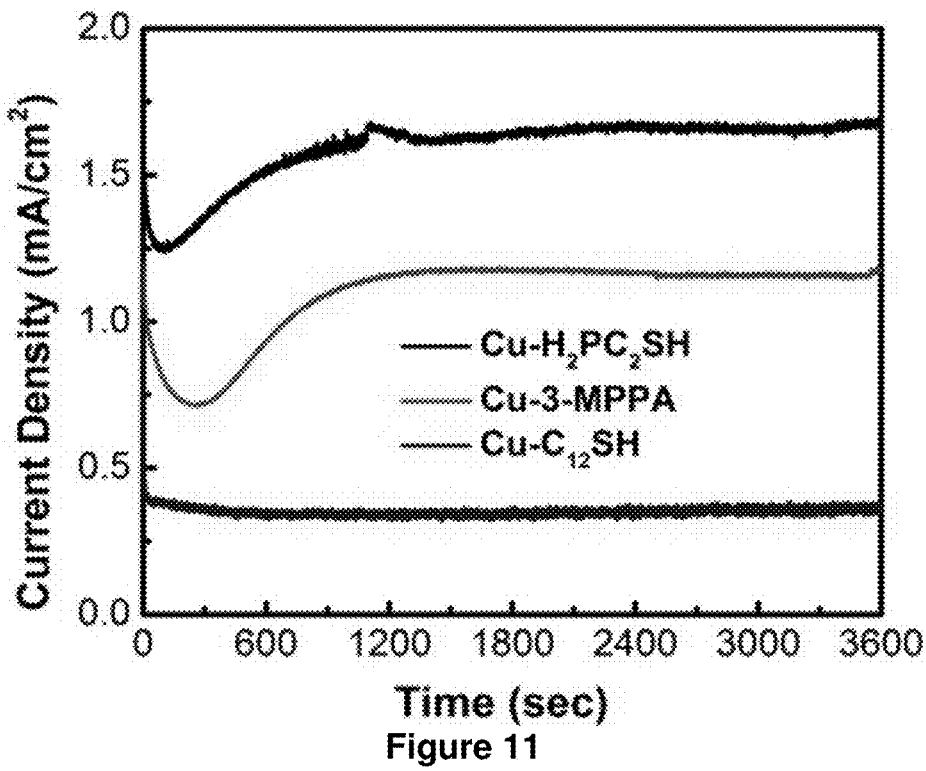

FIG. 11 shows constant potential electrolysis curves of Cu—$H_2PC_2SH$, Cu-3-MPPA and Cu—$Cl_{12}SH$ at a constant potential of –0.55 V vs RHE in CO-saturated 0.1 M KOH.

Figure 12A:
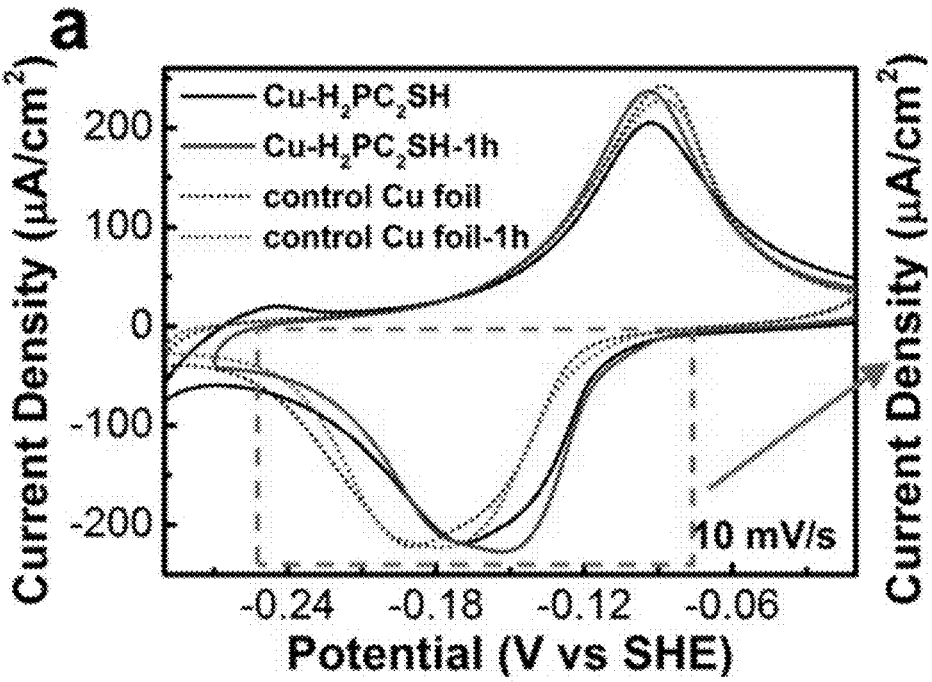

FIG. 12A shows cyclic voltammetry curves of underpotential deposition of Pb on Cu—$H_2PC_2SH$ electrode before (black) and after electrolysis at –0.55 V vs RHE for 1 h (blue) compared to the unfunctionalized Cu foil (dotted black and dotted red). The scan rate is 10 mV/s. Zoomed-in UPD region (dashed green box) shows a constant positive shift of 14 mV upon porphyrin functionalization for both before/after electrolysis.

Figure 12B:
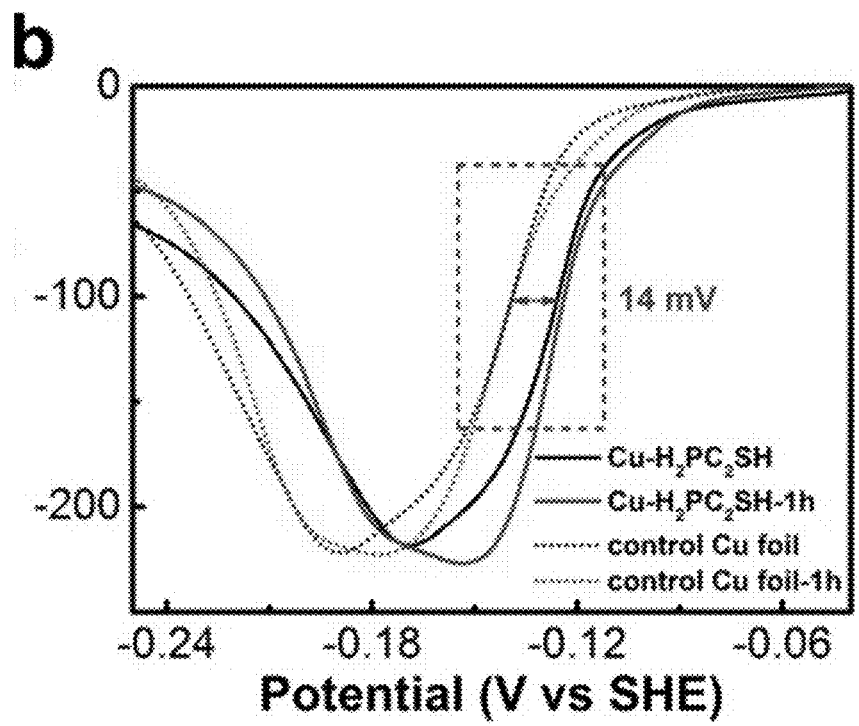

FIG. 12B shows a high resolution N 1s XPS spectra of Cu foil functionalized with porphyrin cages before and after electrolysis at –0.55 V vs RHE for 1 hour (dashed blue line shows the peak of metallic $Cu^0$ and dashed green line shows the peak of oxidized $Cu^{2+}$).

Figure 12C:
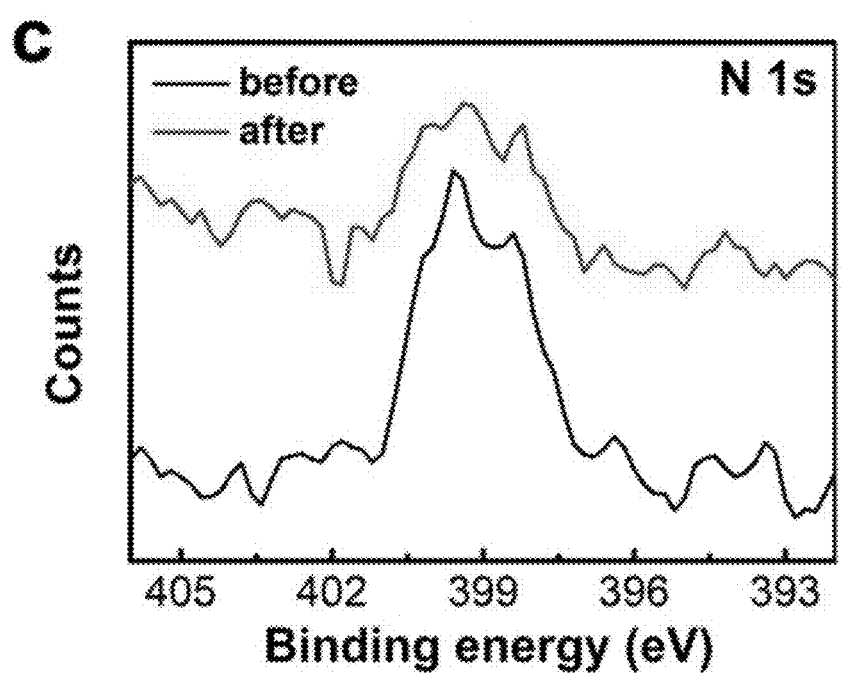

FIG. 12C shows a high resolution S 2p XPS spectra of Cu foil functionalized with porphyrin cages before and after electrolysis at –0.55 V vs RHE for 1 hour (dashed blue line shows the peak of metallic $Cu^0$ and dashed green line shows the peak of oxidized $Cu^{2+}$).

Figure 12D:
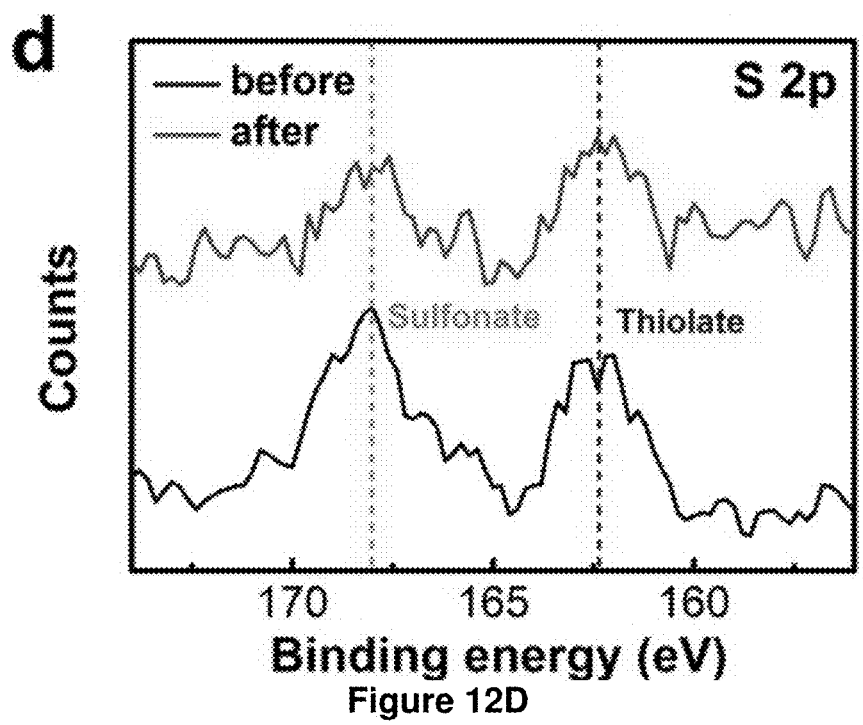

FIG. 12D shows a high resolution Cu 2p XPS spectra of Cu foil functionalized with porphyrin cages before and after electrolysis at −0.55 V vs RHE for 1 hour (dashed blue line shows the peak of metallic $Cu^0$ and dashed green line shows the peak of oxidized $Cu^{2+}$). e) high resolution Cu 2p XPS spectra of treated Cu foil before and after electrolysis at −0.55 V vs RHE for 1 hour.

Figure 12E:
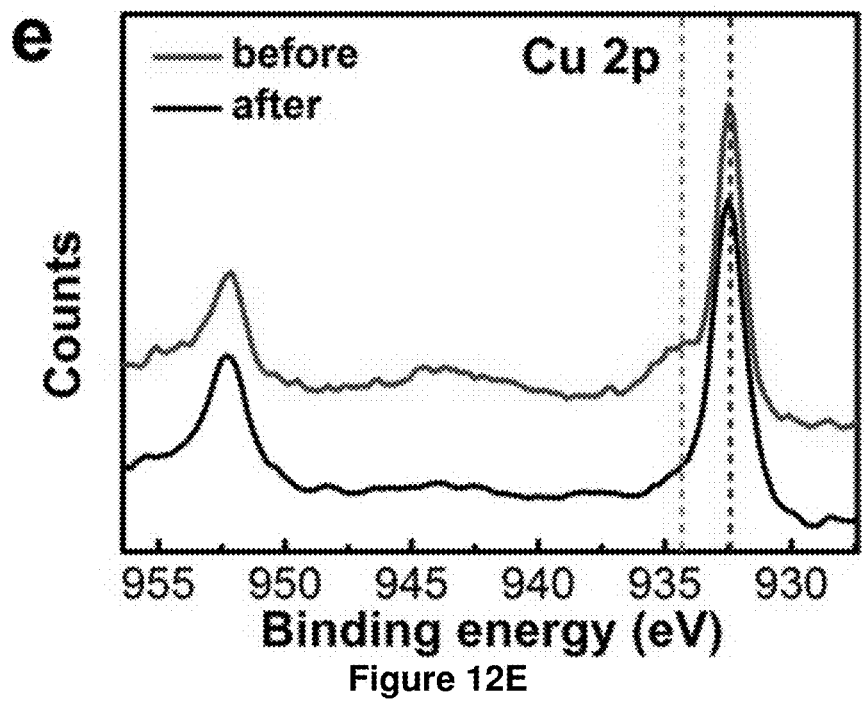

FIG. 12E shows a high resolution Cu 2p XPS spectra of treated Cu foil before and after electrolysis at −0.55 V vs RHE for 1 hour.

Figure 13A:
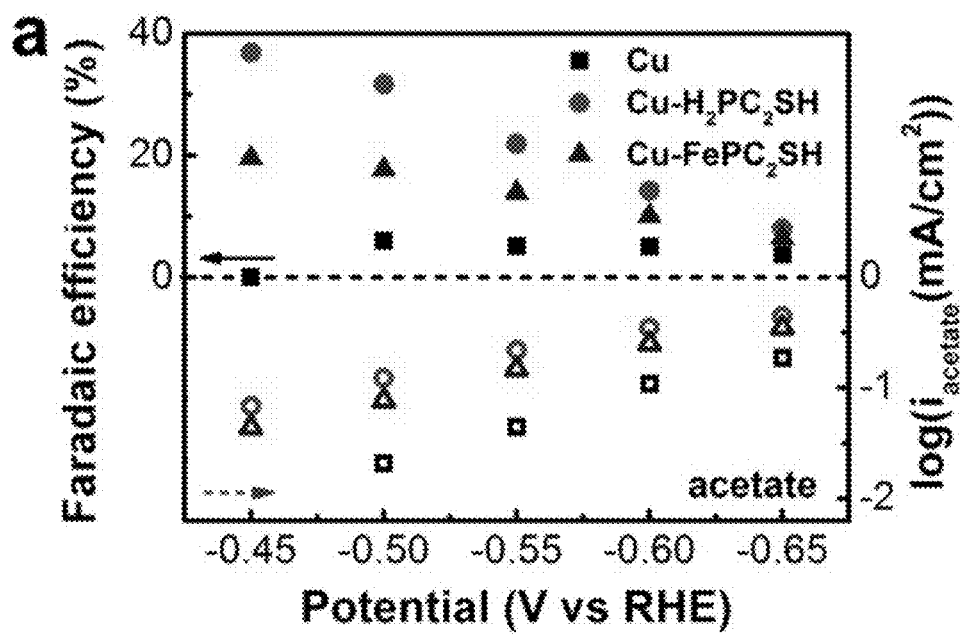

FIG. 13A shows specific faradaic efficiencies and current densities of CO reduction into acetate under different potentials on Cu foil, Cu—$H_2PC_2SH$ and Cu—$FePC_2SH$ in CO-saturated 0.1 M KOH.

Figure 13B:
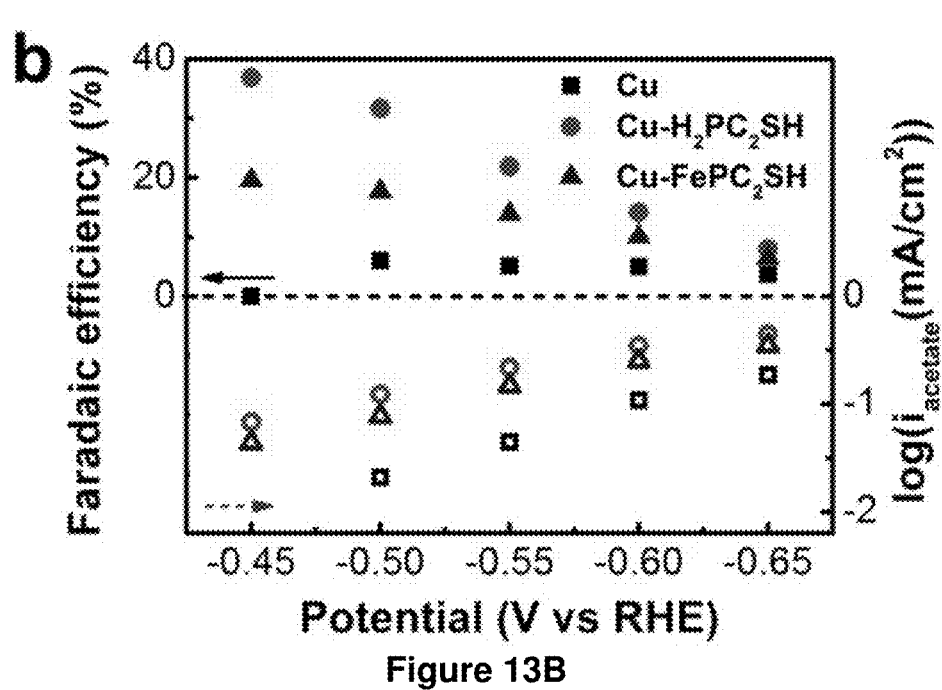

FIG. 13B shows specific faradaic efficiencies and current densities of CO reduction into ethanol under different potentials on Cu foil, Cu—$H_2PC_2SH$ and Cu—$FePC_2SH$ in CO-saturated 0.1 M KOH.

Figure 13C:
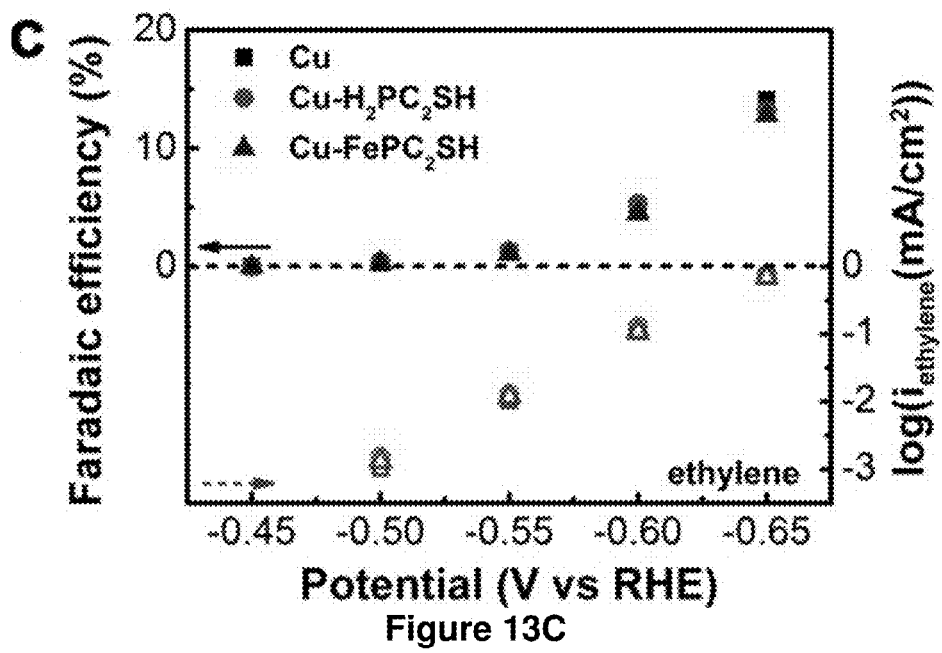

FIG. 13C shows specific faradaic efficiencies and current densities of CO reduction into ethylene under different potentials on Cu foil, Cu—$H_2PC_2SH$ and Cu—$FePC_2SH$ in CO-saturated 0.1 M KOH.

Figure 14A:
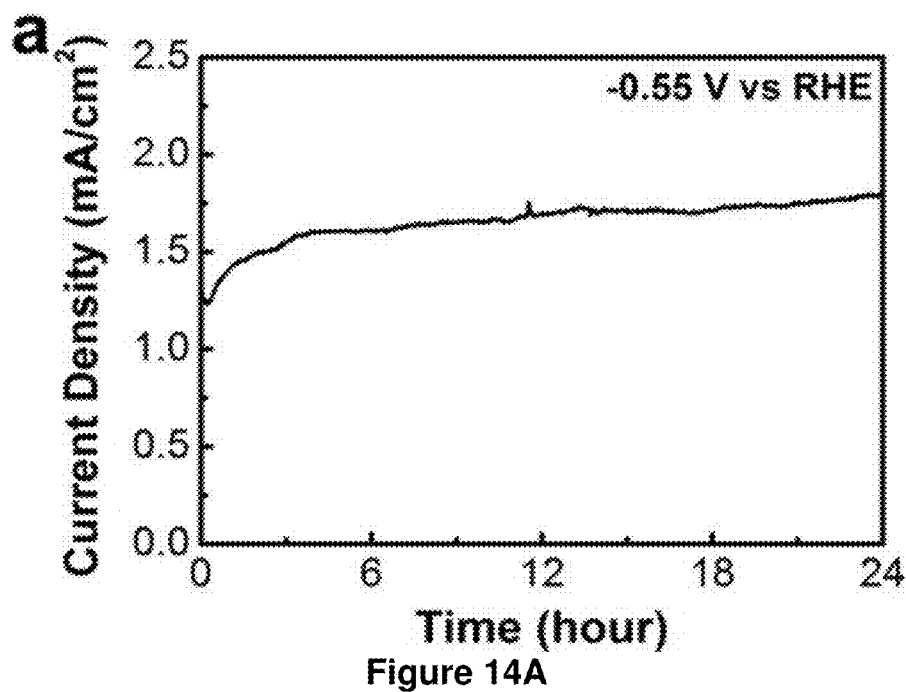

FIG. 14A shows a long-term controlled potential electrolysis curve of Cu—$FePC_2SH$ (based on Cu foil) at a constant potential of −0.55 V vs RHE in CO-saturated 0.1 M KOH.

Figure 14B:
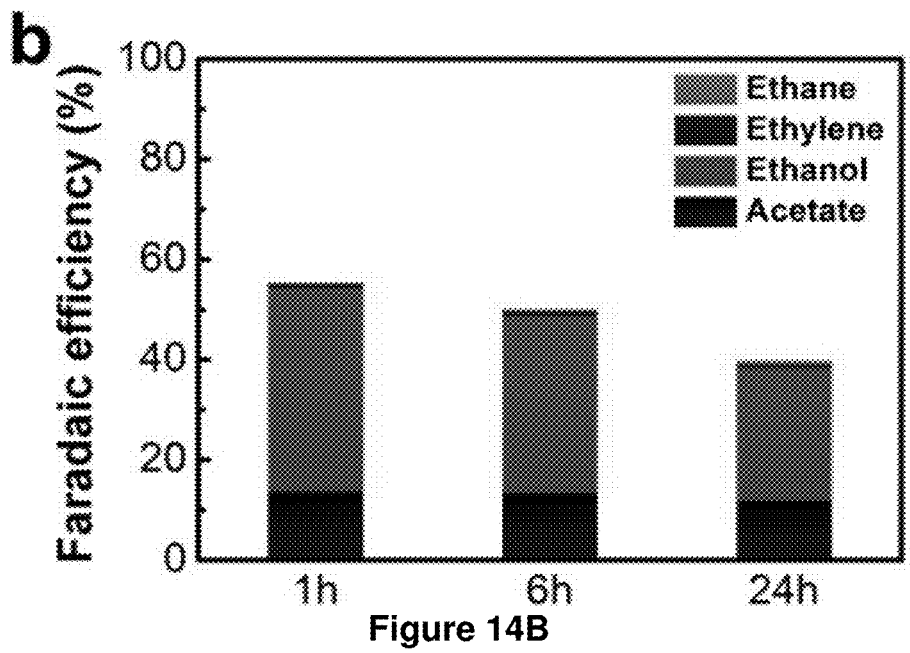

FIG. 14B shows Faradaic efficiencies for CO reduction on Cu—$FePC_2SH$ (based on Cu foil) collected at different time points of long term measurement.

Figure 15A:
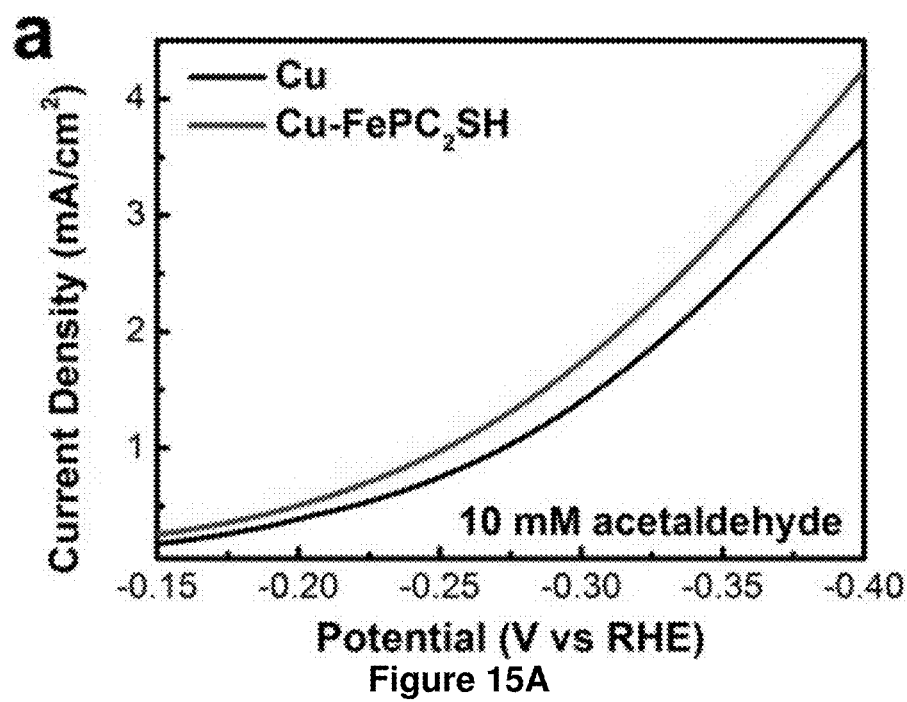

FIG. 15A shows Linear Sweep Voltammetry (LSV) curves of Cu and Cu—$FePC_2SH$ in Ar-saturated 0.1 M KOH+10 mM acetaldehyde.

Figure 15B:
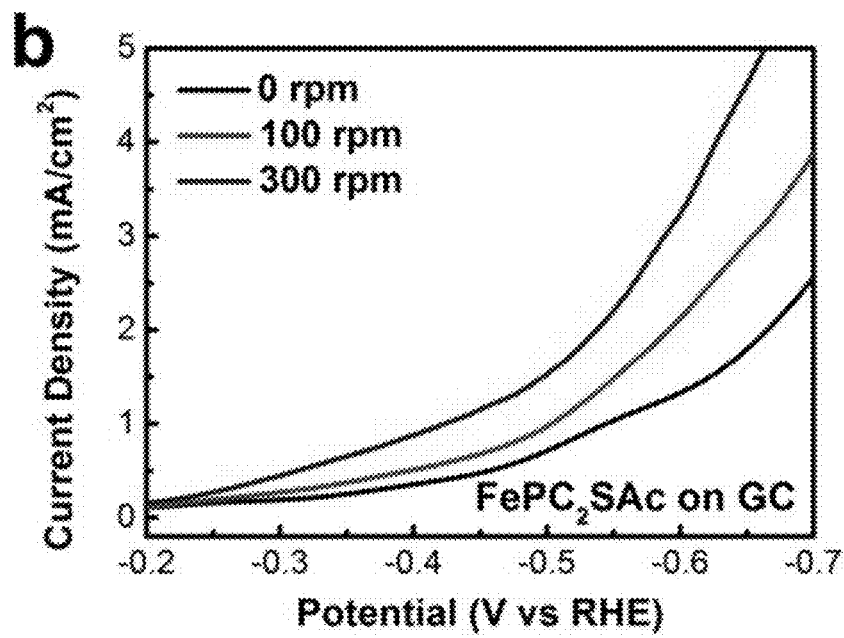

FIG. 15B shows LSV curves of $FePC_2SAc$ on glassy carbon in Ar-saturated 0.1 M KOH+10 mM acetaldehyde under different stirring speed.

Figure 15C:
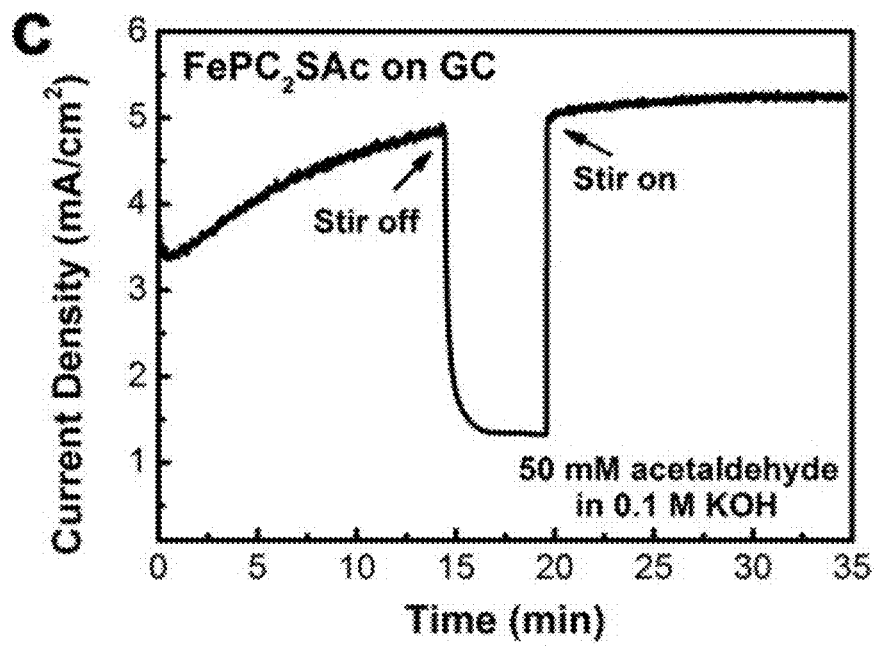

FIG. 15C shows the CPE curve of $FePC_2SAc$ on glassy carbon in Ar-saturated 0.1 M KOH+10 mM acetaldehyde.

Figure 16A:
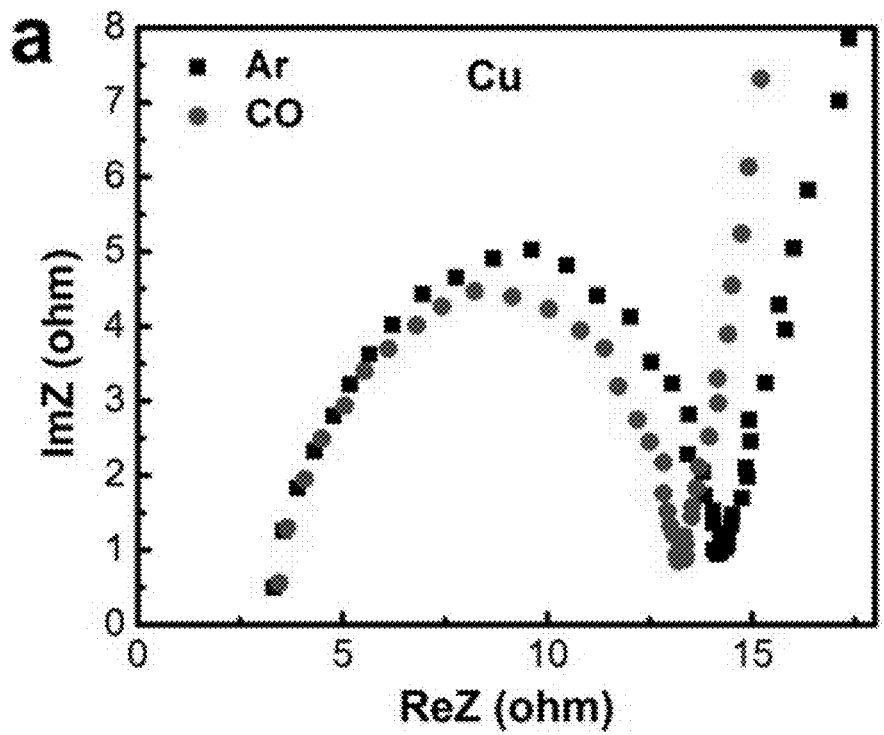

FIG. 16A shows Nyquist plots of Cu under Ar and CO atmosphere in 0.1 M KOH at a constant potential of −0.45 V vs RHE.

Figure 16B:
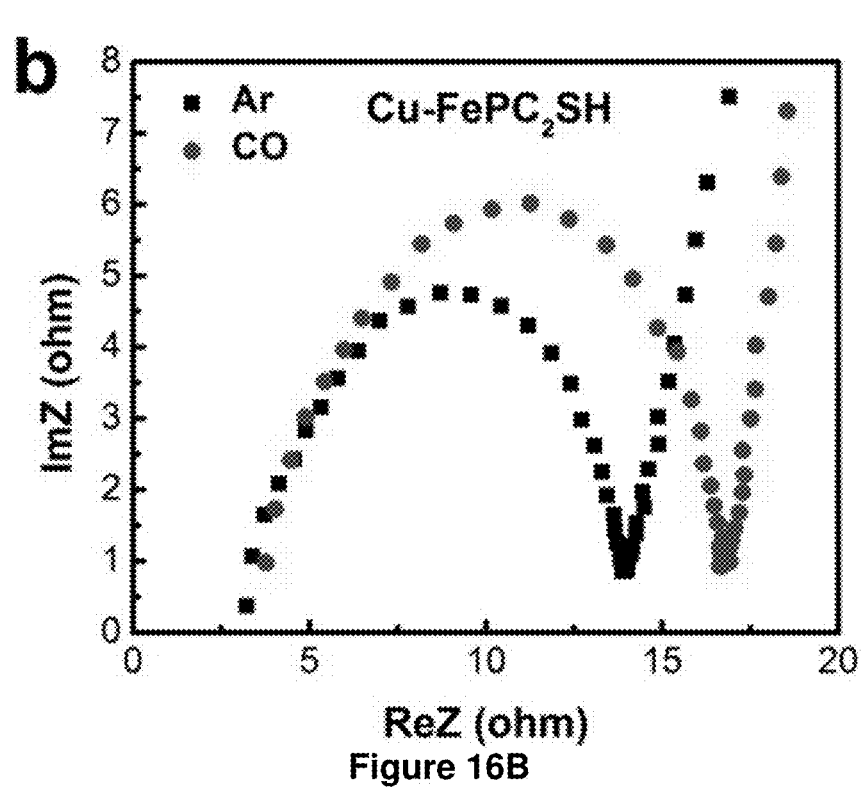

FIG. 16B Nyquist plots of Cu—$FePC_2SH$ under Ar and CO atmosphere in 0.1 M KOH at a constant potential of −0.45 V vs RHE.

Figure 17A:
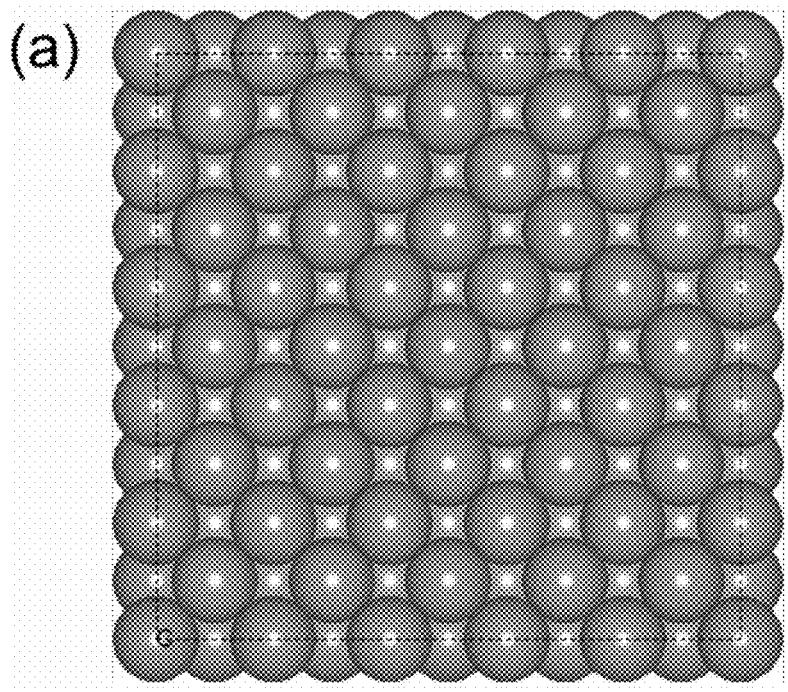

FIG. 17A shows the top view structure of Cu(100).

Figure 17B:
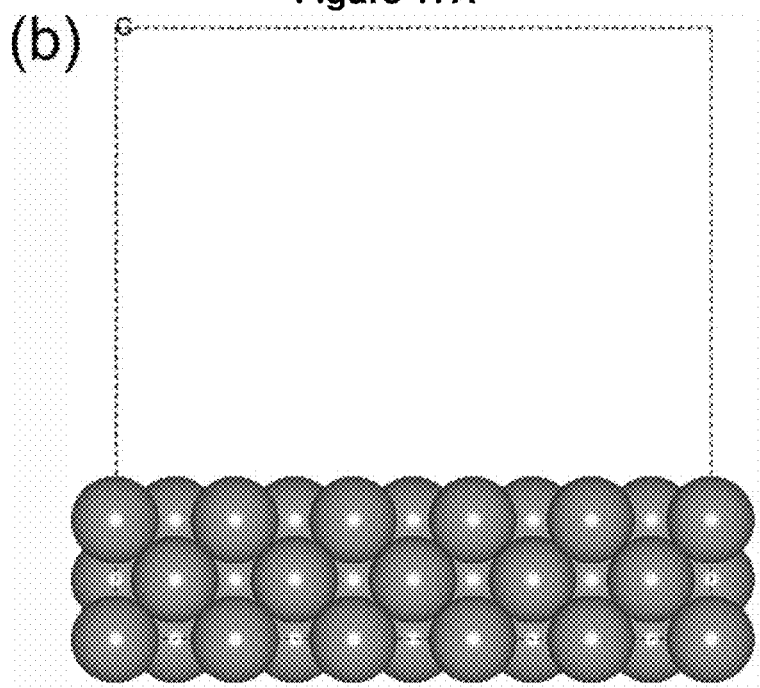

FIG. 17B shows the side view structure of Cu(100).

FIG. 18A shows the top view adsorption configurations of C=C=O on Cu(100).

FIG. 18B shows the side view adsorption configurations of C=C=O on Cu(100).

FIG. 19 shows the adsorption configuration of porphyrin on Cu(100).

DETAILED DESCRIPTION

In the discussions that follow, various process steps may or may not be described using certain types of manufacturing equipment, along with certain process parameters. It is to be appreciated that other types of equipment can be used, with different process parameters employed, and that some of the steps may be performed in other manufacturing equipment without departing from the scope of this invention. Furthermore, different process parameters or manufacturing equipment could be substituted for those described herein without departing from the scope of the invention.

These and other details and advantages of the present invention will become more fully apparent from the following description taken in conjunction with the accompanying drawings.

Figure 1A:
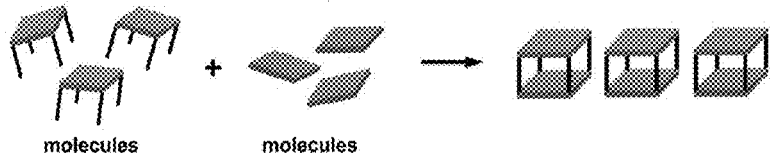
FIG. 1A shows a schematic illustration of traditional supramolecular assembly of cages between molecular components and supramolecular assembly of cages between molecular and materials components, as illustrated by formation of porphyrin cages on electrode surfaces.
Figure 1A:
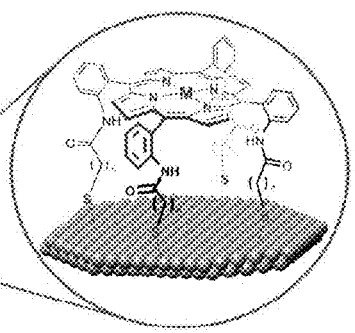
Figure 1B:
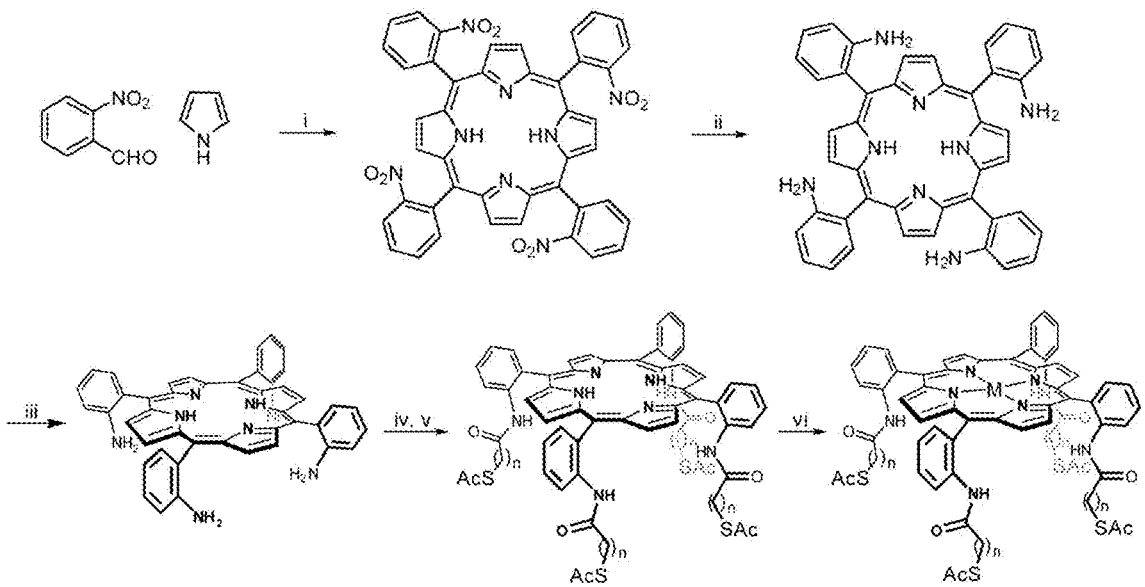
FIG. 1B shows a synthetic procedures for the preparation of thiolate-containing porphyrins: (i) Propionic acid, reflux, 1 h; (ii) $SnCl_2$, 12N HCl, 65° C.; (iii) silica gel, benzene, 80°
Figure 1B:
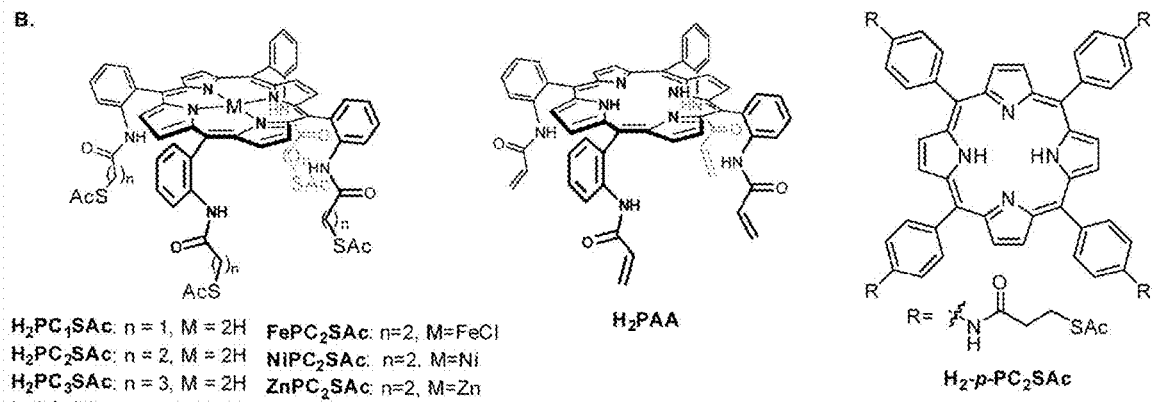

Against this backdrop, we sought to synthesize electrocatalysts for CO reduction that could combine these key bioinorganic features yet allow for molecular-level tunability. We now report a supramolecular approach to CO electrocatalysis in which heterobimetallic cages can be assembled directly at molecular-materials interfaces from nanocrystalline Cu materials,[30-32] but optimizing CO electroreduction catalysts at a molecular level to attain both high specificity and activity remains a significant challenge. In this regard, Nature provides inspiration for CO catalysis in the form of CO dehydrogenase enzymes (CODHs),[34-38] which drive efficient CO catalysis through self-assembly of systematically tunable building blocks. Specifically, we show that metalloporphyrins bearing thiol-terminated organic struts form synthetic cavities of predictable sizes and metal-metal distances upon cofacial interactions with Cu electrodes, enabling electrochemical CO reduction with high selectivity and activity for C2 products (FIGS. 1A and 1B). In addition to introducing interfacial supramolecular chemistry as a versatile design principle for an important catalytic carbon fixation process, this work provides a starting point for merging molecular and materials catalyst components through supramolecular self-assembly for a broader range of chemical transformations and applications.

Applications of the present invention include, but are not limited to:

1. Electrocatalytic Fuel Generation
   1) $CO/CO_2$ reduction into fuels (CO (from $CO_2$), $CH_4$ (methane), $CH_3OH$ (methanol), HCOH (formaldehyde), $C_2H_5OH$ (ethanol), $CH_3COOH$ (acetate or acetic acid), $C_2H_4$ (ethylene), $C_2H_6$ (ethane) and other value-added carbon-based products ($\geq C_2$ product)
   2) Water electrolysis for $H_2$ and $O_2$ generation (proton/water electroreduction into $H_2$ and water electrooxidation into $O_2$)
   3) Electroreduction of $N_2$ into $NH_3$ or other N-containing products
   4) Electroreduction and electrooxidation of abundant biomass or bio-derived resources into high value fuels or chemicals 2. Electrocatalytic Fuel Consumption for Fuel Cells
   1) Electrocatalytic carbon-based fuel oxidation (e.g. methanol oxidation (DMFC), ethanol oxidation (DEFC), methane/ethylene/ethane oxidation)
   2) Electrocatalytic $H_2$ oxidation for $H_2$-based fuel cell (e.g. PEMFC)
   3) Electrocatalytic $O_2$ reduction for fuel cell
   4) Electrocatalytic $NH_3$ oxidation for potential fuel cell 3. Electrocatalytic Sensing or Pollutant Removal
   1) Electrocatalytic nitrate or nitrite reduction
   2) Electrocatalytic phosphate or phosphite reduction
   3) Electrocatalytic organic pollutant sensing and removal
   4) Electrocatalytic glucose sensing for blood sugar detection
   5) Electrochemical toxic gas (hydrogen sulfide, carbon monoxide, phosphene) sensor
   6) Electrochemical $H_2O_2$ sensor 4. Advanced Chemical Transformation using Electrochemical Approach
   1) Electrocatalytic C—H oxidation (aliphatic C—H oxidation and aromatic C—H oxidation)
   2) Electrocatalytic halogenation
   3) Electrocatalytic selective alcohol oxidation and selective ketone/aldehyde/carboxylic acid reduction
   4) Electrocatalytic selective hydrogenation
   5) Electrocatalytic alkene oxidation
   6) Electrocatalytic oxidation of N,S containing compounds (e.g. amines and thiols)
   7) Electrocatalytic reduction of aromatic compounds into saturated rings
   8) Electrocatalytic reduction of nitriles
   9) Electrocatalytic reduction of imines and Schiff bases
   10) Electrocatalytic oxidation of hydrazines into azo compounds or reduction of azo compounds into hydrazines In some embodiments, the composition of the present composition comprises A and B, wherein A is one or more inorganic materials and B is a porous molecule. A and B interact to form one or more cages for catalysis, so A is normally what people use as electrocatalysts, and B is any molecule that can form a cage on top.

TABLE 1

Particular embodiments of A.

| Metals | Metal oxides | Metal chalcogenides (sulfides, selenides, and/or tellurides) | Metal nitrides | Metal phosphides | Metal arsenides |
|---|---|---|---|---|---|
| Mixed metals (including alloys thereof) | Mixed metal oxides | Mixed metal chalcogenides | Mixed metal nitrides | Mixed metal phosphides | Mixed metal arsenides |
| Metal halides | Metal carbides | Metal silicides | Metal borides | Metal oxyhalide | Metal borate |
| Mixed metal halides | Mixed metal carbides | Mixed metal silicides | Mixed metal borides | Metal oxynitride | Metal carbonate |
| Metal phosphate | Metal hydroxide | Carbon | Sulfur | Silicon nitride | Metal hydrides |
| Metal silicate | Metal oxyhydroxide | Silicon | Silicon carbide | Doped carbon | Mixed metal hydrides |

*Mixed metal oxide is $A_xB_yO_z$ (A, B are metals), or more than two metals. For example, bismuth vanadate falls into this category In some embodiments, the metal is a transition metal.

In some embodiments, B is any molecule that can bind to A to form one or more cages through chemical or physical interactions (e.g. covalent bonding, hydrogen bonding, Van der Waals interaction, electrostatic interaction).

In some embodiments, both A and B are catalysts.

Conversion of carbon monoxide (CO), a major one-carbon product of carbon dioxide ($CO_2$) reduction, into value-added multicarbon species is a challenge to addressing global energy demands and climate change. Here we report a modular synthetic approach for aqueous electrochemical CO reduction to carbon-carbon coupled products via self-assembly of supramolecular cages at molecular-materials interfaces. Heterobimetallic cavities formed by face-to-face coordination of thiol-terminated metalloporphyrins to copper electrodes through varying organic struts convert CO to C2 products with high Faradaic efficiency (FE=83% total with 57% to ethanol) and current density (1.34 mA/cm$^2$) at a potential of −0.40 V vs RHE. The cage-functionalized electrodes offer an order of magnitude improvement in both selectivity and activity for electrocatalytic carbon fixation compared to parent copper surfaces or copper functionalized with porphyrins in an edge-on orientation.

RESULTS AND DISCUSSION

Design, Synthesis, and Characterization of Porphyrin Caps for Formation of Supramolecular Cages at Molecule-Materials Interfaces.

The design and synthesis of cage-forming porphyrin caps and their assembly onto metal surfaces are depicted in FIG. 1A. We reasoned that α, α, α, α-atropisomers inspired by the classic picket-fence porphyrin model for hemoglobin oxygen transport[39] would provide a rigid platform to promote a face-to-face arrangement between the porphyrin molecule and metal surface, where thiol-terminated legs built off of the porphyrin scaffold at the ortho positions of the 5,10,15,20 aryl groups serve as multidentate connecting points to bind to the copper electrode material. Self-assembly at the molecular-materials interface would form a cage in which the porphyrin sits like a molecular table on top of the metal surface floor (FIG. 1A). Accordingly, systematic variation of linkers and metals in both the molecular and materials components of this supramolecular assembly provide an opportunity to explore and optimize catalytic structures and properties. This hybrid approach, where interfacial supramolecular architectures are derived from both molecular and materials building blocks, is complementary to discrete molecular organic cages[40-44] as well as extended porous materials bearing catalytic porphyrin units.[23,45-50]

A general route to the syntheses of α, α, α, α-porphyrins and their metallated derivatives is shown in Scheme 1A. Scheme 1B depicts the molecular structures and nomenclatures of the synthesized (metallo)porphyrins along with two porphyrin analogs employed as controls.[51,52] In particular, we synthesized an isostructural α, α, α, α-porphyrin with legs that lack terminal thiol pendants for surface binding, as well as a para-substituted tetrathiol porphyrin congener designed to favor edge-on rather than face-to-face interactions with the metal surface. Full synthetic details are given in Supporting Information.

To generate hybrid supramolecular cages at the molecular-materials interface, metallic copper surfaces were treated with thiol porphyrins generated from in situ deprotection of thioacetate counterparts (FIG. 2A).[53] Well-defined metallic Cu films prepared by e-beam evaporation were utilized as a model substrate for surface characterization[54]. The successful attachment of the porphyrins to the Cu surface was first evidenced by high-resolution N1s and S2p X-ray photoelectron spectroscopy (XPS). The N1s peak is consistent with a previously reported spectrum assigned to a porphyrin monolayer, confirming the existence of porphyrins on the surface (FIG. 2B).[55-56] The S2p region exhibits two distinct peaks at around ~161-164 eV and ~167-169 eV, corresponding to the thiolate and sulfonate species, respectively (FIG. 2C).[54] The presence of thiolate species on the surface corroborates possible porphyrin attachment via formation of Cu—S bonds, whereas the sulfonate peaks might be derived from partial thiolate oxidation after air exposure due to the high oxygen permeability of the void spaces in the porphyrin cages. The functionalized Cu surface also shows a slightly wider Cu 2p peak but with lower signal at ~933 eV compared to the unfunctionalized Cu control surface (FIGS. 7A-B), which can be reasoned by the surface-attached porphyrin partially oxidizing Cu surface via Cu—S bond formation. Complementary external reflection Fourier transform infrared spectroscopy (FTIR) measurements provide addition support for porphyrin attachment (FIG. 8).

Two potential limiting configurations for porphyrin coordination to the Cu surface may be envisioned, which are anticipated to lead to disparate catalytic performances. In one possible configuration, the porphyrin coordinates with the Cu surface via Cu—S interactions to form a cage architecture where the porphyrin face is elevated above the surface. Another possibility is for the porphyrin face to lie directly on the Cu surface through van der Waals interactions, blocking potential access of reactants to the surface. To investigate these possible binding modes, we employed electrochemical underpotential deposition (UPD) studies, in which the measured monolayer thickness of a metal-deposited guest is highly indicative of the number of surface substrate sites that are electrochemically accessible.[57] Porphyrins that orient face-down and promote direct interactions with the Cu surface would block the electrode and result in fewer Cu sites able to be accessed by UPD. In contrast, porphyrins that orient with legs down and favor coordination through Cu—S bonds to create porous cages would leave more Cu sites accessible to the electrolyte solution, resulting in UPD peak areas that are comparable to control Cu surfaces.

To this end, we probed accessible Cu sites by the UPD of lead (Pb) on Cu surfaces in the presence of chloride anions. The standard Cu surfaces (100 nm Cu on Si) show a pair of underpotential deposition and dissolution peaks in the range of −0.05 V to −0.25 V vs standard hydrogen electrode (SHE) (FIG. 2D).[58] Treating the Cu surfaces with $H_2$-PAA porphyrins bearing terminal alkene groups show voltammograms that exhibit smaller peak areas with retained peak shapes and potentials, likely due to the inability of the alkenes to form stable interactions with the Cu surface and possible porphyrin-Cu stacking behavior, both of which would impede Pb deposition. In contrast, the Cu surfaces functionalized with $H_2PC_2SH$ porphyrins bearing terminal thiol groups exhibit almost identical peak areas to control Cu (FIG. 2D), showing that porphyrins interacting in this mode do not restrict access to the Cu electrode. Interestingly, the thiol-porphyrin-functionalized Cu surfaces also exhibit a distinct peak shift to more positive potentials, indicating more facile Pb deposition with this molecular attachment (FIG. 2D). Taken together, the data suggest that the local electronic structure of the Cu surface has been altered after porphyrin binding, likely due to the partial oxidation of the surface as a result of the formation of Cu—S bonds. The UPD results also imply a high coverage of the porphyrin molecules on the Cu surface since no UPD current is observed at the potential characteristic for unfunctionalized Cu surfaces. The observations from UPD and XPS studies both support the creation of porphyrin cages on a sterically accessible metallic Cu surface via designed Cu—S interactions.

Electrocatalytic CO Reduction with Hybrid Supramolecular Porphyrin Cages Formed on Copper. With these initial hybrid systems in hand, we evaluated their activity for electrocatalytic CO reduction compared to unfunctionalized Cu foils (FIGS. 3A-3F). To compare catalytic activity and selectivity, with particular interest in C—C coupled products, controlled potential electrolysis (CPE) measurements at various potentials were carried out in CO-saturated 0.1 M KOH (aq). The collected gas-phase products were analyzed by gas chromatography (GC) and the liquid-phase products were quantified by $^1$H-NMR (FIG. 9). Three major C2 products derived from C—C bond formation—acetate, ethanol and ethylene—were detected for all electrodes in the potential range of −0.45 V to −0.65 V vs reversible hydrogen electrode (RHE). The faradaic efficiencies (FEs) and specific current densities for each product are shown for direct comparison (FIGS. 3A-3F). As expected, Cu foil alone exhibits low basal activity, with <15% total FE towards CO reduction at relatively low overpotentials (<−0.6 V vs RHE) (FIGS. 3A-3D and FIGS. 10A and 10B) and an appreciable amount of ethylene as the major product of CO reduction beyond −0.6 V vs RHE, consistent with previous reports (FIGS. 3E and 3F).[30,33]

We next evaluated the effects of porphyrin functionalization as well as cage size on CO reduction to C—C coupled products by systematically varying the linker lengths in the spacer region ($H2PC_nSH$, n=1-4). Interestingly, all Cu foils with surface-tethered porphyrins exhibit significantly higher propensities for oxygenate formation (FIGS. 4A-4B). Specifically, an optimal CO reduction selectivity towards oxygenate production was obtained with the two-carbon linker at a potential of −0.55 V vs RHE (FIG. 4B). Further expanding the cage size (n=3, 4) results in a notable decrease in the FEs towards $C_2$ oxygenates. We then compared the activity and selectivity of the optimized Cu—$H_2PC_2SH$ electrode with bare Cu foil under different potentials, and the results show significantly higher FEs and more positive onset potentials for $C_2$ oxygenate formation. More negative applied potentials greatly influence the observed FEs, resulting in reduced amounts of acetate and ethanol production while boosting undesired competitive hydrogen evolution. In contrast, almost identical FEs and current densities were observed on Cu foil and Cu—$H_2PC_2SH$ electrodes for the production of ethylene (FIGS. 3E and 3F), suggesting that the surface-tethered porphyrin cages affect the reduction pathways toward C2 oxygenate products but not the reduction pathway to this C2 hydrocarbon.

To further probe the nature of the observed enhancements in CO selectivity enabled by supramolecular formation of porphyrin cages on Cu surfaces, we designed a series of control molecules to investigate the roles of these surface-tethered porphyrin caps. Cu surfaces functionalized with simple monothiol additives such as 1-dodecanethiol ($C_{12}SH$), which support conventional self-assembled monolayers (SAMs)[54], or with 3-mercapto-N-phenylpropanamide (3-MPPA), which mimics a single linker arm in $H_2PC_2SH$ porphyrins with a pendant amide, were first utilized as thiolate analogs for comparison. The Cu—$C_{12}SH$ electrode exhibits dramatically lowered current densities compared to Cu—$H_2PC_2SH$, with hydrogen ($H_2$) as the only major product generated at a potential of −0.55 V vs RHE (FIGS. 5A and 11). We speculate that this low activity for CO reduction is likely the result of the large energy barrier for diffusing polar CO molecules into the densely packed nonpolar SAMs. Along the same lines, Cu-3-MPPA exhibits lower overall current densities compared to Cu-tethered thiolporphyrins and a characteristic CPE curve with an initial drop followed by a gradual recovery in current density similar to Cu—$H_2PC_2SH$ electrode (FIGS. 5A and 11). However, the selectivity for this MPPA system towards CO reduction is low, reaching only a ~10% total FE for carbon products (FIG. 3A). Moreover, the para-functionalized porphyrin analog (Cu—$H_2$-p-$PC_2SH$) also exhibits significantly lower selectivity towards CO reduction compared to the table-like ortho analog Cu—$H_2$-o-$PC_2SH$ (FIG. 5A). We speculate that the para porphyrins having a flat architecture would either pack by standing edge-on the Cu surfaces via one or two thiolate linkages, or lie flat on the surface with direct face-to-face stacking; in either case, these porphyrins are incapable of forming catalytic cages and serve to block accessible Cu sites, thereby lowering electrocatalytic activity and CO selectivity. Finally, the Cu-H$_2$PAA system bearing terminal alkenes that do not strongly bind copper, mentioned above for UPD studies, exhibits a similar product distribution to bare Cu surfaces (FIG. 5A) and reduced surface access as measured by UPD (FIG. 2D).

The foregoing results establish that the supramolecular cavity created by the rigid table-like porphyrin scaffold plays a central role in enhancing the selectivity for electrochemical CO reduction to value-added C2 products and over competing water reduction, whereas traditional architectures for molecular functionalization of surfaces through metal-thiol interactions are not beneficial due to the lack of accessible sites on the Cu electrodes. Density functional theory (DFT) calculations on a Cu(100) surface point to a tentative mechanistic proposal involving a ketene intermediate,[59,60] which we speculate may be tuned through hydrogen-bond interactions with the porphyrin cap (FIG. 5B and Table 2). Such interactions could rationalize the observed differences in selectivity for CO reduction observed for varying cage sizes, but does not rule out other plausible mechanistic possibilities and further studies must be pursued to address this open question.

The stability of the porphyrin cages on the Cu surfaces was further investigated by UPD and XPS studies (FIGS. 12A-12F). Cu—H$_2$PC$_2$SH electrode shows a consistent positive shift of the UPD peak by ~14 mV compared to the unfunctionalized control Cu electrode. This positive shift is retained after electrolysis, suggesting the persistence of the porphyrin cages on Cu surfaces under CO electroreduction conditions (FIGS. 12A and 12B). XPS measurements reveal slight decreases of N 1 s and S 2p XPS signals and an increase of Cu 2p XPS signal after electrolysis, indicating some loss of weakly-bound porphyrin cages during electrocatalysis (FIGS. 12C-12E), but the retained N 1 s and S 2p peaks still suggest the relatively high stability of the porphyrin cages for CO reduction.

Heterobimetallic Supramolecular Porphyrin Cages for Improved CO Reduction Reactivity. In addition to enforcing a rigid cage to maintain surface accessibility as well as orient hydrogen-bond pendants to influence reaction selectivity, the porphyrin caps also enable facile introduction and tuning of a second metal site in proximity to the metal electrode center. We anticipated that a second type of metal center has the potential not only to participate as a catalytically active site but also to contribute as a synergistic cofactor to increase local CO concentrations and/or tune the electronic structure of the metal surface for improved CO reduction activity. Indeed, metalloporphyrins have been explored widely in homogeneous catalysis.[14,19,24,61-64] To this end, we screened a series of metals inserted into the two-carbon-linker porphyrin caps (e.g., Fe, Ni, Zn) and observed that the introduction of Fe centers in the porphyrins increases the preference for ethanol production while decreasing the relative ratio of acetate at all potentials applied (FIGS. 6A, 6B and 13A-13C). An optimal ethanol FE of ~52% is obtained on a Cu—FePC$_2$SH electrode at a potential of −0.50 V vs RHE (FIG. 6B) with good long-term stability over continuous CO reduction electrocatalysis (FIGS. 14A and 14B), only losing ca. 10% FE for C2 products over a 24 h period. As expected, functionalization with the redox-inert Zn porphyrin shows comparable product selectivity to that of free-base porphyrins. In contrast, insertion of Ni into porphyrin cap shifts product distributions toward hydrogen formation and a higher FE for ethylene, which may likely be due to the high intrinsic hydrogenation capability of the Ni porphyrins (FIG. 6A).[65,66]

With the observation of varying product distributions with different metal substitutions into the porphyrin cap, we next sought to probe aspects of how the Fe derivative promotes higher levels of ethanol production. In this context, previous studies have identified acetaldehyde as a key intermediate for electrochemical CO reduction into ethanol in alkaline media[67]. We thus utilized acetaldehyde as a model substrate for studying the role of Fe in this catalytic process. To this end, the electrocatalytic reductions of acetaldehyde on bare Cu foil, Cu—H$_2$PC$_2$SH, and Cu—FePC$_2$SH electrodes were examined in 0.1 M KOH (aq) with the addition of 10 mM acetaldehyde under Ar atmosphere. The Cu—FePC$_2$SH electrode shows slightly higher activity towards acetaldehyde reduction, with a positive shift in the polarization curves (FIGS. 15A-15C) and much higher FEs towards ethanol production than bare Cu surfaces or Cu functionalized with free-base porphyrin caps (FIG. 6C). In fact, Fe porphyrins alone deposited on glassy carbon electrodes show moderate activity toward acetaldehyde reduction with a reasonable current density within the potential range for CO reduction (FIGS. 15A-15C), which is consistent with previous findings that Fe porphyrins can be effectively used as catalysts for the hydrogenation of various aldehydes and ketones.[68] As such, we propose that Fe porphyrins might participate in reduction of acetaldehyde intermediates, which in turn favors increased ethanol production in electrochemical CO reduction. Indeed, the Tafel plot of the specific ethanol current densities on Cu—FePC$_2$SH electrodes shows a much earlier onset potential but exhibits a larger Tafel slope of 174 mV/dec (FIG. 6D). This deviation from the Tafel slopes of 126 and 127 mV/dec observed on Cu foil and on Cu—H$_2$PC$_2$SH electrodes, respectively, supports the participation of Fe porphyrins in the rate-determining step of the ethanol production pathway, with observation of a larger Tafel slope for the Fe—Cu bimetallic system compared to Cu-only congeners resulting from inefficiencies in charge transfer between the Fe porphyrin and Cu surface. Evidence for this notion is provided by the larger charge transfer resistance under CO atmosphere compared to Ar (FIGS. 16A and 16B), and future efforts will aim to increase charge transfer efficiency.

Finally, we sought to optimize the CO reduction activity of these hybrid heterobimetallic systems, using the Cu—FePC$_2$SH porphyrin catalyst showing the best product selectivity toward the liquid fuel ethanol as a starting point. Previous work highlights the significance of exposed Cu facets for electrochemical CO$_2$ or CO reductions[26,60,69-74] where Cu(100) or other high-energy facets are more active than the thermodynamically more stable Cu(111) surfaces and can enhance formation of CO dimerized products.[26,60,71,73,75,76] We employed electrodeposition of Cu on glassy carbon in chloride-containing aqueous CuSO$_4$ electrolyte as a general and facile way of controlling the exposed facets of the Cu substrates.[77-78] The supramolecular catalyst systems formed by combination of the FePC$_2$SH porphyrin caps with electrodeposited Cu exhibit markedly higher specific current densities at low overpotentials (FIG. 6F). The CO reduction product distribution is relatively similar to that of Fe porphyrin cages on Cu foils, but with slightly lower FEs for hydrogen production (FIG. 6E). The higher current densities allow for quantitative analyses of the products at even lower overpotentials where competitive hydrogen evolution is insignificant. Specifically, at −0.4 V vs RHE, the catalyst achieves a total FE of 83% towards CO reduction into C$_2$ products, with 57% FE for ethanol and 24% FE for acetate at a current density of 1.34 mA/cm² (FIG. 6E).

CONCLUSIONS

In summary, we have presented a supramolecular strategy for electrocatalytic carbon fixation to multicarbon products through the self-assembly of synthetic cages at molecular-materials interfaces. Porphyrin capping units with directional legs terminated by thiol ligands form face-to-face cavities upon binding copper electrodes that leave surface sites electrochemically accessible. Varying linker lengths as well as metal substitutions in the porphyrin core provide versatile molecular handles for tuning selectivity and activity for electrochemical CO reduction to carbon-carbon coupled products. The heterobimetallic molecular-materials catalyzed formed by assembly of the C2-linked Fe porphyrin derivative on Cu achieves up to 83% FE for CO reduction into C2 products, with up to 57% ethanol and 24% acetate generated at −0.4 V vs RHE and a current density of 1.34 mA/cm². These values represent an order of magnitude improvement over unfunctionalized copper electrodes. Further experiments suggest that the Fe center can aid in cooperative reduction of potential acetaldehyde intermediates. Moreover, control analogs that lack thiol binding groups as well as positional isomers favoring edge-on binding or direct Van der Waals stacking exhibit reduced surface access and negligible CO over proton reduction selectivity, pointing to a critical role for the three-dimensional pocket in catalysis. In addition to establishing a unique electrochemical platform for reducing CO to value-added $C_2$ oxygenates, this work provides a starting point for the design of supramolecular architectures at molecular-materials interfaces for a broader range of chemical transformations and applications of interest.

The following documents are attached to this Provisional Application, and are incorporated herein by reference as if fully set out in their entirety.

REFERENCES CITED (1) Lewis, N. S.; Nocera, D. G. Powering the planet: Chemical challenges in solar energy utilization. *Proc. Natl. Acad. Sci. U.S.A.* 2006, 103 (43), 15729.
(2) Gray, H. B. Powering the planet with solar fuel. *Nat. Chem.* 2009, 1 (1), 7.
(3) Kumar, B.; Llorente, M.; Froehlich, J.; Dang, T.; Sathrum, A.; Kubiak, C. P. Photochemical and photoelectrochemical reduction of CO2. *Annu. Rev. Phys. Chem.* 2012, 63, 541.
(4) Appel, A. M.; Bercaw, J. E.; Bocarsly, A. B.; Dobbek, H.; DuBois, D. L.; Dupuis, M.; Ferry, J. G.; Fujita, E.; Hille, R.; Kenis, P. J. A.; Kerfeld, C. A.; Morris, R. H.; Peden, C. H. F.; Portis, A. R.; Ragsdale, S. W.; Rauchfuss, T. B.; Reek, J. N. H.; Seefeldt, L. C.; Thauer, R. K.; Waldrop, G. L. Frontiers, Opportunities, and Challenges in Biochemical and Chemical Catalysis of $CO_2$ Fixation. *Chem. Rev.* 2013, 113 (8), 6621.
(5) Costentin, C.; Robert, M.; Savéant, J.-M. Catalysis of the electrochemical reduction of carbon dioxide. *Chem. Soc. Rev.* 2013, 42 (6), 2423.
(6) Elgrishi, N.; Chambers, M. B.; Wang, X.; Fontecave, M. Molecular polypyridine-based metal complexes as catalysts for the reduction of CO 2. *Chem. Soc. Rev.* 2017, 46 (3), 761.
(7) Liu, M.; Pang, Y. J.; Zhang, B.; De Luna, P.; Voznyy, O.; Xu, J. X.; Zheng, X. L.; Dinh, C. T.; Fan, F. J.; Cao, C. H.; de Arquer, F. P. G.; Safaei, T. S.; Mepham, A.; Klinkova, A.; Kumacheva, E.; Filleter, T.; Sinton, D.; Kelley, S. O.; Sargent, E. H. Enhanced electrocatalytic $CO_2$ reduction via field-induced reagent concentration. *Nature* 2016, 537 (7620), 382.
(8) Fisher, B. J.; Eisenberg, R. Electrocatalytic reduction of carbon dioxide by using macrocycles of nickel and cobalt. *J. Am. Chem. Soc* 1980, 102 (24), 7361.
(9) Hawecker, J.; Lehn, J.-M.; Ziessel, R. Electrocatalytic reduction of carbon dioxide mediated by Re (bipy)(CO) 3 Cl (bipy=2, 2'-bipyridine). *J. Chem. Soc., Chem. Commun.* 1984, (6), 328.
(10) Hori, Y.; Kikuchi, K.; Suzuki, S. Production of CO and $CH_4$ in electrochemical reduction of $CO_2$ at metal electrodes in aqueous hydrogencarbonate solution. *Chem. Lett.* 1985, 14 (11), 1695.
(11) Beley, M.; Collin, J. P.; Ruppert, R.; Sauvage, J. P. Electrocatalytic reduction of carbon dioxide by nickel cyclam2+ in water: study of the factors affecting the efficiency and the selectivity of the process. *J. Am. Chem. Soc* 1986, 108 (24), 7461.
(12) Rosen, B. A.; Salehi-Khojin, A.; Thorson, M. R.; Zhu, W.; Whipple, D. T.; Kenis, P. J.; Masel, R. I. Ionic liquid-mediated selective conversion of $CO_2$ to CO at low overpotentials. *Science* 2011, 334 (6056), 643.
(13) Thoi, V. S.; Chang, C. J. Nickel N-heterocyclic carbene-pyridine complexes that exhibit selectivity for electrocatalytic reduction of carbon dioxide over water. *Chem. Commun.* 2011, 47 (23), 6578.
(14) Costentin, C.; Drouet, S.; Robert, M.; Savéant, J.-M. A local proton source enhances $CO_2$ electroreduction to CO by a molecular Fe catalyst. *Science* 2012, 338 (6103), 90.
(15) Schneider, J.; Jia, H.; Kobiro, K.; Cabelli, D. E.; Muckerman, J. T.; Fujita, E. Nickel (II) macrocycles: highly efficient electrocatalysts for the selective reduction of CO 2 to CO. *Energy Environ. Sci.* 2012, 5 (11), 9502.
(16) Smieja, J. M.; Sampson, M. D.; Grice, K. A.; Benson, E. E.; Froehlich, J. D.; Kubiak, C. P. Manganese as a substitute for rhenium in $CO_2$ reduction catalysts: The importance of acids. *Inorg. Chem.* 2013, 52 (5), 2484.
(17) Thoi, V. S.; Kornienko, N.; Margarit, C. G.; Yang, P.; Chang, C. J. Visible-Light Photoredox Catalysis: Selective Reduction of Carbon Dioxide to Carbon Monoxide by a Nickel N-Heterocyclic Carbene-Isoquinoline Complex. *J. Am. Chem. Soc* 2013, 135 (38), 14413.
(18) Zhu, W.; Michalsky, R.; Metin, Ö.; Lv, H.; Guo, S.; Wright, C. J.; Sun, X.; Peterson, A. A.; Sun, S. Monodisperse Au nanoparticles for selective electrocatalytic reduction of $CO_2$ to CO. *J. Am. Chem. Soc* 2013, 135 (45), 16833.
(19) Costentin, C.; Passard, G.; Robert, M.; Saveant, J.-M. Ultraefficient homogeneous catalyst for the $CO_2$-to-CO electrochemical conversion. *Proc. Natl. Acad. Sci. U.S.A.* 2014, 111 (42), 14990.
(20) Kim, D.; Resasco, J.; Yu, Y.; Asiri, A. M.; Yang, P. Synergistic geometric and electronic effects for electrochemical reduction of carbon dioxide using gold-copper bimetallic nanoparticles. *Nat. Commun.* 2014, 5, 4948.
(21) Zhu, W.; Zhang, Y.-J.; Zhang, H.; Lv, H.; Li, Q.; Michalsky, R.; Peterson, A. A.; Sun, S. Active and selective conversion of $CO_2$ to CO on ultrathin Au nanowires. *J. Am. Chem. Soc* 2014, 136 (46), 16132.
(22) Hall, A. S.; Yoon, Y.; Wuttig, A.; Surendranath, Y. Mesostructure-induced selectivity in $CO_2$ reduction catalysis. *J. Am. Chem. Soc* 2015, 137 (47), 14834.
(23) Lin, S.; Diercks, C. S.; Zhang, Y. B.; Kornienko, N.; Nichols, E. M.; Zhao, Y. B.; Paris, A. R.; Kim, D.; Yang,

(24) Azcarate, I.; Costentin, C.; Robert, M.; Savéant, J.-M. Through-Space Charge Interaction Substituent Effects in Molecular Catalysis Leading to the Design of the Most Efficient Catalyst of $CO_2$-to-CO Electrochemical Conversion. *J. Am. Chem. Soc* 2016, 138 (51), 16639.

(25) Cao, Z.; Kim, D.; Hong, D. C.; Yu, Y.; Xu, J.; Lin, S.; Wen, X. D.; Nichols, E. M.; Jeong, K.; Reimer, J. A.; Yang, P. D.; Chang, C. J. A Molecular Surface Functionalization Approach to Tuning Nanoparticle Electrocatalysts for Carbon Dioxide Reduction. *J. Am. Chem. Soc* 2016, 138 (26), 8120.

(26) Wang, Z.; Yang, G.; Zhang, Z.; Jin, M.; Yin, Y. Selectivity on Etching: Creation of High-Energy Facets on Copper Nanocrystals for $CO_2$ Electrochemical Reduction. *ACS nano* 2016, 10 (4), 4559.

(27) Hong, D.; Tsukakoshi, Y.; Kotani, H.; Ishizuka, T.; Kojima, T. Visible-Light-Driven Photocatalytic $CO_2$ Reduction by a Ni (II) Complex Bearing a Bioinspired Tetradentate Ligand for Selective CO Production. *J. Am. Chem. Soc* 2017, 139 (19), 6538.

(28) Iglesia, E. Design, synthesis, and use of cobalt-based Fischer-Tropsch synthesis catalysts. *Appl. Catal., A* 1997, 161 (1-2), 59.

(29) Khodakov, A. Y.; Chu, W.; Fongarland, P. Advances in the development of novel cobalt Fischer-Tropsch catalysts for synthesis of long-chain hydrocarbons and clean fuels. *Chem. Rev.* 2007, 107 (5), 1692.

(30) Li, C. W.; Ciston, J.; Kanan, M. W. Electroreduction of carbon monoxide to liquid fuel on oxide-derived nanocrystalline copper. *Nature* 2014, 508 (7497), 504.

(31) Verdaguer-Casadevall, A.; Li, C. W.; Johansson, T. P.; Scott, S. B.; McKeown, J. T.; Kumar, M.; Stephens, I. E.; Kanan, M. W.; Chorkendorff, I. Probing the active surface sites for CO reduction on oxide-derived copper electrocatalysts. *J. Am. Chem. Soc* 2015, 137 (31), 9808.

(32) Feng, X.; Jiang, K.; Fan, S.; Kanan, M. W. A direct grain-boundary-activity correlation for CO electroreduction on Cu nanoparticles. *ACS central science* 2016, 2 (3), 169.

(33) Hori, Y.; Murata, A.; Takahashi, R.; Suzuki, S. Electroreduction of carbon monoxide to methane and ethylene at a copper electrode in aqueous solutions at ambient temperature and pressure. *J. Am. Chem. Soc* 1987, 109 (16), 5022.

(34) Drennan, C. L.; Heo, J.; Sintchak, M. D.; Schreiter, E.; Ludden, P. W. Life on carbon monoxide: X-ray structure of Rhodospirillum rubrum Ni—Fe—S carbon monoxide dehydrogenase. *Proc. Natl. Acad. Sci. U.S.A.* 2001, 98 (21), 11973.

(35) Dobbek, H.; Gremer, L.; Kiefersauer, R.; Huber, R.; Meyer, O. Catalysis at a dinuclear [CuSMo (O) OH] cluster in a CO dehydrogenase resolved at 1.1-Å resolution. *Proc. Natl. Acad. Sci. U.S.A.* 2002, 99 (25), 15971.

(36) Reda, T.; Plugge, C. M.; Abram, N. J.; Hirst, J. Reversible interconversion of carbon dioxide and formate by an electroactive enzyme. *Proc. Natl. Acad. Sci. U.S.A.* 2008, 105 (31), 10654.

(37) Cracknell, J. A.; Vincent, K. A.; Armstrong, F. A. Enzymes as working or inspirational electrocatalysts for fuel cells and electrolysis. *Chem. Rev.* 2008, 108 (7), 2439.

(38) Woolerton, T. W.; Sheard, S.; Reisner, E.; Pierce, E.; Ragsdale, S. W.; Armstrong, F. A. Efficient and clean photoreduction of $CO_2$ to CO by enzyme-modified TiO2 nanoparticles using visible light. *J. Am. Chem. Soc* 2010, 132 (7), 2132.

(39) Collman, J. P.; Zhang, X.; Wong, K.; Brauman, J. I. Dioxygen binding in iron and cobalt picnic basket porphyrins. *J. Am. Chem. Soc* 1994, 116 (14), 6245.

(40) Anderson, H. L.; Sanders, J. K. Synthesis of a cyclic porphyrin trimer with a semi-rigid cavity. *J. Chem. Soc., Chem. Commun.* 1989, (22), 1714.

(41) Anderson, H. L.; Sanders, J. K. Amine-Template-Directed Synthesis of Cyclic Porphyrin Oligomers. *Angew. Chem., Int. Ed.* 1990, 29 (12), 1400.

(42) Hong, S.; Rohman, M.; Jia, J.; Kim, Y.; Moon, D.; Kim, Y.; Ko, Y. H.; Lee, E.; Kim, K. Porphyrin boxes: rationally designed porous organic cages. *Angew. Chem., Int. Ed.* 2015, 54 (45), 13241.

(43) Benke, B. P.; Aich, P.; Kim, Y.; Kim, K. L.; Rohman, M. R.; Hong, S.; Hwang, I.-C.; Lee, E. H.; Roh, J. H.; Kim, K. Iodide-Selective Synthetic Ion Channels Based on Shape-persistent Organic Cages. *J. Am. Chem. Soc* 2017, 139 (22), 7432.

(44) Cooper, A. I. Porous Molecular Solids and Liquids. *ACS central science* 2017, 3 (6), 544.

(45) Shultz, A. M.; Farha, O. K.; Hupp, J. T.; Nguyen, S. T. A catalytically active, permanently microporous MOF with metalloporphyrin struts. *J. Am. Chem. Soc* 2009, 131 (12), 4204.

(46) Lee, C. Y.; Farha, O. K.; Hong, B. J.; Sarjeant, A. A.; Nguyen, S. T.; Hupp, J. T. Light-harvesting metal-organic frameworks (MOFs): efficient strut-to-strut energy transfer in bodipy and porphyrin-based MOFs. *J. Am. Chem. Soc* 2011, 133 (40), 15858.

(47) Hod, I.; Sampson, M. D.; Deria, P.; Kubiak, C. P.; Farha, O. K.; Hupp, J. T. Fe-porphyrin-based metal-organic framework films as high-surface concentration, heterogeneous catalysts for electrochemical reduction of CO2. *ACS Catal.* 2015, 5 (11), 6302.

(48) Kornienko, N.; Zhao, Y.; Kley, C. S.; Zhu, C.; Kim, D.; Lin, S.; Chang, C. J.; Yaghi, O. M.; Yang, P. Metal-organic frameworks for electrocatalytic reduction of carbon dioxide. *J. Am. Chem. Soc* 2015, 137 (44), 14129.

(49) Wan, S.; Gandara, F.; Asano, A.; Furukawa, H.; Saeki, A.; Dey, S. K.; Liao, L.; Ambrogio, M. W.; Botros, Y. Y.; Duan, X. F.; Seki, S.; Stoddart, J. F.; Yaghi, O. M. Covalent Organic Frameworks with High Charge Carrier Mobility. *Chem. Mater.* 2011, 23 (18), 4094.

(50) Smith, B. J.; Parent, L. R.; Overholts, A. C.; Beaucage, P. A.; Bisbey, R. P.; Chavez, A. D.; Hwang, N.; Park, C.; Evans, A. M.; Gianneschi, N. C.; Dichtel, W. R. Colloidal Covalent Organic Frameworks. *ACS central science* 2017, 3 (1), 58.

(51) Ohyama, J.; Hitomi, Y.; Higuchi, Y.; Tanaka, T. Size controlled synthesis of gold nanoparticles by porphyrin with four sulfur atoms. *Top. Catal.* 2009, 52 (6-7), 852.

(52) Hitomi, Y.; Aoki, K.; Miyachi, R.; Ohyama, J.; Kodera, M.; Tanaka, T.; Sugihara, F. Gold Nanoparticles Coated with Manganese-Porphyrin That Effectively Shorten the Longitudinal Relaxation Time of Water Molecules Depending on the Particle Size. *Chem. Lett.* 2014, 43 (12), 1901.

(53) Pakiari, A.; Jamshidi, Z. Nature and strength of M-S Bonds (M=Au, Ag, and Cu) in binary alloy gold clusters. *The J. Phys. Chem. A* 2010, 114 (34), 9212.

(54) Laibinis, P. E.; Whitesides, G. M. Self-assembled monolayers of n-alkanethiolates on copper are barrier films that protect the metal against oxidation by air. *J. Am. Chem. Soc* 1992, 114 (23), 9022.

(55) Gassman, P. G.; Ghosh, A.; Almlof, J. Electronic effects of peripheral substituents in porphyrins: x-ray photoelectron spectroscopy and ab initio self-consistent field calculations. *J. Am. Chem. Soc* 1992, 114 (25), 9990.

(56) Lal, C.; Caputo, M.; Goldoni, A.; Jain, I. Conformational adaptation of 2H-Tetraphenylporphyrin at Fe/Si (100) interface during metalation. *J. Mater. Res. Technol.* 2014, 3 (1), 42.

(57) Herrero, E.; Buller, L. J.; Abruña, H. D. Underpotential deposition at single crystal surfaces of Au, Pt, Ag and other materials. *Chem. Rev.* 2001, 101 (7), 1897.

(58) Brisard, G. M.; Zenati, E.; Gasteiger, H. A.; Markovic, N.; Ross Jr, P. N. Underpotential deposition of lead on Copper (111): A study using a single-crystal rotating ring disk electrode and ex situ low-energy electron diffraction and scanning tunneling microscopy. *Langmuir* 1995, 11 (6), 2221.

(59) Xiao, H.; Cheng, T.; Goddard, W. A. Atomistic Mechanisms Underlying Selectivities in C1 and C2 Products from Electrochemical Reduction of CO on Cu (111). *J. Am. Chem. Soc* 2017, 139 (1), 130.

(60) Cheng, T.; Xiao, H.; Goddard, W. A. Full atomistic reaction mechanism with kinetics for CO reduction on Cu (100) from ab initio molecular dynamics free-energy calculations at 298 K. *Proc. Natl. Acad. Sci. U.S.A.* 2017, 114 (8), 1795.

(61) Kellett, R. M.; Spiro, T. G. Cobalt (I) porphyrin catalysts of hydrogen production from water. *Inorg. Chem.* 1985, 24 (15), 2373.

(62) Liu, W.; Huang, X.; Cheng, M.-J.; Nielsen, R. J.; Goddard, W. A.; Groves, J. T. Oxidative aliphatic CH fluorination with fluoride ion catalyzed by a manganese porphyrin. *Science* 2012, 337 (6100), 1322.

(63) Kleingardner, J. G.; Kandemir, B.; Bren, K. L. Hydrogen evolution from neutral water under aerobic conditions catalyzed by cobalt microperoxidase-11. *J. Am. Chem. Soc* 2013, 136 (1), 4.

(64) McLaughlin, M. P.; Retegan, M.; Bill, E.; Payne, T. M.; Shafaat, H. S.; Pena, S.; Sudhamsu, J.; Ensign, A. A.; Crane, B. R.; Neese, F.; Holland, P. L. Azurin as a Protein Scaffold for a Low-coordinate Nonheme Iron Site with a Small-molecule Binding Pocket. *J. Am. Chem. Soc* 2012, 134 (48), 19746.

(65) Bediako, D. K.; Solis, B. H.; Dogutan, D. K.; Roubelakis, M. M.; Maher, A. G.; Lee, C. H.; Chambers, M. B.; Hammes-Schiffer, S.; Nocera, D. G. Role of pendant proton relays and proton-coupled electron transfer on the hydrogen evolution reaction by nickel hangman porphyrins. *Proc. Natl. Acad. Sci. U.S.A.* 2014, 111 (42), 15001.

(66) Han, Y. Z.; Fang, H. Y.; Jing, H. Z.; Sun, H. L.; Lei, H. T.; Lai, W. Z.; Cao, R. Singly versus Doubly Reduced Nickel Porphyrins for Proton Reduction: Experimental and Theoretical Evidence for a Homolytic Hydrogen-Evolution Reaction. *Angew. Chem., Int. Ed.* 2016, 55 (18), 5457.

(67) Bertheussen, E.; Verdaguer-Casadevall, A.; Ravasio, D.; Montoya, J. H.; Trimarco, D. B.; Roy, C.; Meier, S.; Wendland, J.; Norskov, J. K.; Stephens, I. E. L.; Chorkendorff, I. Acetaldehyde as an Intermediate in the Electroreduction of Carbon Monoxide to Ethanol on Oxide-Derived Copper. *Angew. Chem., Int. Ed.* 2016, 55 (4), 1450.

(68) Junge, K.; Schroder, K.; Beller, M. Homogeneous catalysis using iron complexes: recent developments in selective reductions. *Chem. Commun.* 2011, 47 (17), 4849.

(69) Schouten, K.; Kwon, Y.; Van der Ham, C.; Qin, Z.; Koper, M. A new mechanism for the selectivity to C 1 and C 2 species in the electrochemical reduction of carbon dioxide on copper electrodes. *Chem. Sci.* 2011, 2 (10), 1902.

(70) Roberts, F. S.; Kuhl, K. P.; Nilsson, A. High selectivity for ethylene from carbon dioxide reduction over copper nanocube electrocatalysts. *Angew. Chem., Int. Ed.* 2015, 54 (17), 5179.

(71) Luo, W.; Nie, X.; Janik, M. J.; Asthagiri, A. Facet Dependence of $CO_2$ Reduction Paths on Cu Electrodes. *ACS Catal.* 2015, 6 (1), 219.

(72) Loiudice, A.; Lobaccaro, P.; Kamali, E. A.; Thao, T.; Huang, B. H.; Ager, J. W.; Buonsanti, R. Tailoring Copper Nanocrystals towards C2 Products in Electrochemical $CO_2$ Reduction. *Angew. Chem., Int. Ed.* 2016, 55 (19), 5789.

(73) Pérez-Gallent, E.; Figueiredo, M. C.; Calle-Vallejo, F.; Koper, M. Spectroscopic Observation of a Hydrogenated CO Dimer Intermediate During CO Reduction on Cu (100) Electrodes. *Angew. Chem., Int. Ed.* 2017, 129 (13), 3675.

(74) Li, Y.; Cui, F.; Ross, M. B.; Kim, D.; Sun, Y.; Yang, P. Structure-Sensitive $CO_2$ Electroreduction to Hydrocarbons on Ultrathin 5-fold Twinned Copper Nanowires. *Nano Lett.* 2017, 17 (2), 1312.

(75) Schouten, K. J. P.; Qin, Z.; Gallent, E. P. r.; Koper, M. T. Two pathways for the formation of ethylene in CO reduction on single-crystal copper electrodes. *J. Am. Chem. Soc* 2012, 134 (24), 9864.

(76) Kim, Y.-G.; Javier, A.; Baricuatro, J. H.; Torelli, D.; Cummins, K. D.; Tsang, C. F.; Hemminger, J. C.; Soriaga, M. P. Surface reconstruction of pure-Cu single-crystal electrodes under CO-reduction potentials in alkaline solutions: A study by seriatim ECSTM-DEMS. *J Electroanal. Chem.* 2016, 780, 290.

(77) Lakshmanan, V.; Mackinnon, D.; Brannen, J. The effect of chloride ion in the electrowinning of copper. *J. Appl. Electrochem.* 1977, 7 (1), 81.

(78) Shao, W.; Zangari, G. Dendritic growth and morphology selection in copper electrodeposition from acidic sulfate solutions containing chlorides. *J. Phys. Chem. C* 2009, 113 (23), 10097.

Supramolecular porphyrin cages assembled at molecular-materials interfaces for electrocatalytic CO reduction.

Experimental Section

1. Synthesis and Materials

α,α,α,α,-Tetrakis-aminophenylporphyrin and 3-mercapto-N-phenylpropanamide were synthesized according to the published literatures[1-3]. Tetrakis-p-aminophenylporphyrin was purchased from Frontier Scientific. Graphite rod (>99.9995%), Cu foil (99.99%, 1 mm thickness) and glassy carbon rod (1 mm diameter) was purchased from Alfa Aesar. De-ionized water was from a Millipore Autopure system.

Carbon monoxide (4.5 UHP) and Argon (5.0 UHP) gas were purchased from Praxair. All other chemicals were purchased from Sigma Aldrich. All reagents were of analytical grade and used without further purification.

2. Instrumentation $^1$H NMR and $^{13}$C NMR spectra were collected in CDCl3 (Cambridge Isotope Laboratories, Cambridge, Mass.) at 25° C. on Bruker AVB-400 with $^{13}$C operating frequencies of 101 MHz at the College of Chemistry NMR Facility at the University of California, Berkeley. All chemical shifts are reported in the standard notation of parts per million relative to residual solvent peak at 7.26 ppm (CDCl$_3$) and as an internal reference[4]. Splitting patterns are indicated as follows: br, broad; s, singlet; d, doublet; t, triplet; m, multiplet; dd, doublet of doublets. $^1$H NMR spectra of the liquid-phase CO reduction production were analyzed at 25° C. on Bruker AV-500. A 0.5-ml sample of the liquid was mixed with 0.1 ml D$_2$O and 1.67 parts per million dimethyl sulfoxide (DMSO) as the internal standard. Electrospray mass spectral analyses were carried out using a LC-MS (Agilent Technology 6130, Quadrupole LC/MS). High resolution mass spectral analyses (ESI-MS) were carried out at the College of Chemistry Mass Spectrometry Facility at the University of California, Berkeley. X-ray photoelectron spectroscopy was performed using an ultra-high vacuum (UHV) PHI 5400 XPS system with a non-monochromatic Mg X-ray source (K$\alpha$=1253.6 eV) operated at 350 W power. Fourier-transform infrared spectroscopy (FTIR) was acquired on a Thermo Scientific Nicolet 6700 FTIR spectrometer. E-beam evaporation was carried out in SEC-600/SE-600 High Vacuum Deposition Systems from CHA industries.

3. General Procedures for the Synthesis of H$_2$PC$_n$SAc (n=1-4) and MPC$_2$SAc 0.1 mmol α,α,α,α,-Tetrakis-aminophenylporphyrin (0.075 g) was dissolved in dry THF (10 mL) and 12 eq. diethylaniline (214 μl) was added. N$_2$ was flushed for 10 min and the vessel was plunged in an ice-bath until the temperature of the solution reached 0° C. (15 min). 8 equiv. bromoacetylbromide (0.88 mmol, 77 μL) in solution in dichloromethane (2 mL) were introduced dropwise over 30 s to the stirred mixture at 0° C. After stirring for 30 min at 0° C., 20 equiv. potassium thioacetate (253 mg) was added, and the reaction mixture was stirred at room temperature for another 4 hours. The solvent was then removed under reduced pressure, and the product was purified by flash column chromatography (silica gel, dichloromethane/ethyl acetate). 3-bromopropionyl bromide, 4-chlorobutyryl chloride and 5-chlorovaleroyl chloride were utilized for synthesizing H$_2$PC$_2$SAc, H$_2$PC$_3$SAc and H$_2$PC$_4$SAc respectively. The stirring procedure in the H$_2$PC$_3$SAc and H$_2$PC$_4$SAc synthesis was replaced by stirring for 4 hours at 25° C. Metallation of the H$_2$PC$_2$SAc (M=Fe, Ni, Zn) was carried out according to published procedures.[5] The para-functionalized porphyrin analog (H$_2$-p-PC$_2$SAc) was synthesized with identical procedure to the general procedure using tetrakis-p-aminophenylporphyrin as the precursor.

H$_2$PC$_1$SAc, Synthesized according to the general procedure. Purple solid; $^1$H NMR (500 MHz, CDCl$_3$) δ 8.79 (s, 8H), 8.58 (d, J=8.4 Hz, 4H), 8.00 (d, J=7.6 Hz, 4H), 7.85 (td, J=8.0, 1.6 Hz, 4H), 7.64 (s, 4H), 7.54 (t, J=7.5 Hz, 4H), 2.73 (s, 8H), 0.74 (s, 12H), -2.64 (s, 2H); $^{13}$C NMR (101 MHz, CDCl$_3$) δ 194.12, 165.94, 138.18, 134.64, 131.83, 131.55, 129.94, 123.64, 121.82, 114.81, 77.39, 33.25, 28.77.; MS (HR-ESI) m/z cal'd C$_{60}$H$_{50}$N$_8$O$_8$S$_4$ [M+H]$^+$ 1139.2731, found 1139.2746. The structure of H$_2$PC$_1$SAc is:

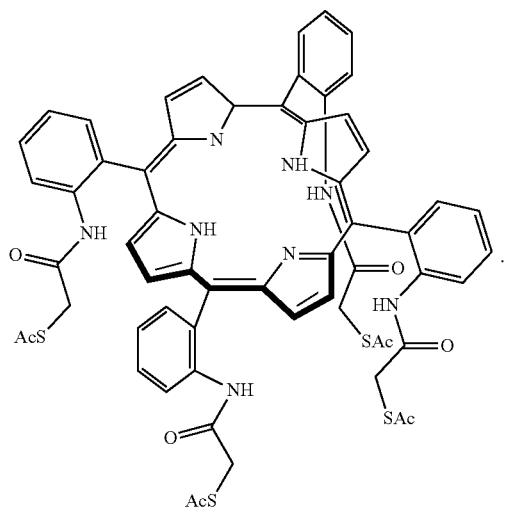

H$_2$PC$_2$SAc, Synthesized according to the general procedure. Purple solid; $^1$H NMR (500 MHz, Chloroform-d) δ 8.82 (s, 8H), 8.65 (d, J=8.5 Hz, 4H), 7.93 (d, J=7.5 Hz, 4H), 7.85 (td, J=8.0, 1.6 Hz, 4H), 7.53 (t, J=7.5 Hz, 4H), 7.13 (s, 4H), 2.55 (t, J=6.7 Hz, 8H), 1.71 (t, J=6.7 Hz, 8H), 1.62 (s, 12H), -2.74 (s, 2H). $^{13}$C NMR (101 MHz, CDCl$_3$) δ 195.58, 168.89, 138.10, 135.07, 131.85, 131.35, 130.03, 123.53, 122.09, 115.09, 35.93, 29.97, 24.41.; MS (HR-ESI) m/z cal'd C$_{64}$H$_{57}$N$_8$O$_8$S$_4$ [M+H]$^+$ 1195.3339, found 1195.3331; Fe(PC$_2$SAc)Cl MS (HR-ESI) m/z cal'd C$_{64}$H$_{57}$N$_8$O$_8$S$_4$Fe [M-Cl]$^+$ 1248.2453, found 1248.2468; NiPC$_2$SAc MS (HR-ESI) m/z cal'd C$_{64}$H$_{57}$N$_8$O$_8$S$_4$Ni [M+H]$^+$ 1251.2536, found 1251.2531; ZnPC$_2$SAc MS (HR-ESI) m/z cal'd C$_{64}$H$_{57}$N$_8$O$_8$S$_4$Zn [M+H]$^+$ 1257.2474, found 1257.2478. H$_2$PC$_3$SAc, Synthesized according to the general procedure. Purple solid; $^1$H NMR (500 MHz, Chloroform-d) δ 8.89 (s, 8H), 8.69 (d, J=8.5 Hz, 4H), 7.93 (d, J=7.5 Hz, 4H), 7.91-7.85 (m, 4H), 7.54 (t, J=7.5 Hz, 4H), 2.24 (t, J=7.7 Hz, 8H), 1.76 (s, 12H), 1.55 (t, J=7.2 Hz, 8H), 1.44 (m, 8H), -2.70 (s, 2H); $^{13}$C NMR (101 MHz, CDCl$_3$) δ 195.11, 170.15, 138.15, 135.36, 131.96, 131.49, 129.98, 123.49, 122.18, 115.33, 35.70, 30.09, 27.76, 25.02.; MS (HR-ESI) m/z cal'd C$_{68}$H$_{67}$N$_8$O$_8$S$_4$ [M+H]$^+$ 1251.3965, found 1251.3969. The structure of H$_2$PC$_2$SAc is:

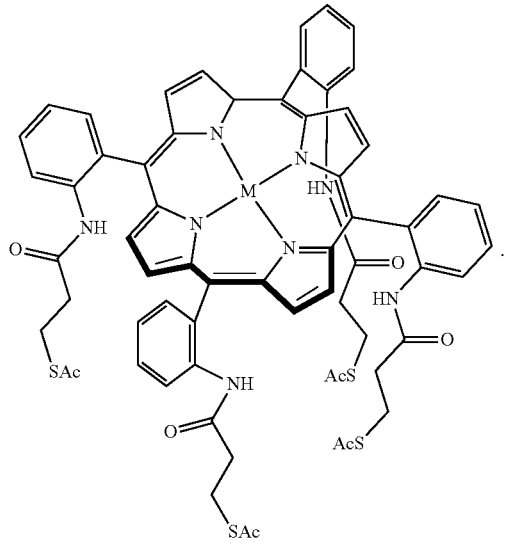

M = 2 H, FeCl, Ni, Zn

H₂PC₃SAc, Synthesized according to the general procedure. Purple solid; 1H NMR (500 MHz, Chloroform-d) δ 8.89 (s, 8H), 8.69 (d, J=8.5 Hz, 4H), 7.93 (d, J=7.5 Hz, 4H), 7.91-7.85 (m, 4H), 7.54 (t, J=7.5 Hz, 4H), 2.24 (t, J=7.7 Hz, 8H), 1.76 (s, 12H), 1.55 (t, J=7.2 Hz, 8H), 1.44 (m, 8H), −2.70 (s, 2H); 13C NMR (101 MHz, CDCl₃) δ 195.11, 170.15, 138.15, 135.36, 131.96, 131.49, 129.98, 123.49, 122.18, 115.33, 35.70, 30.09, 27.76, 25.02.; MS (HR-ESI) m/z cal'd $C_{68}H_{67}N_8O_8S_4$ [M+H]⁺ 1251.3965, found 1251.3969. The structure of H₂PC₃SAc is:

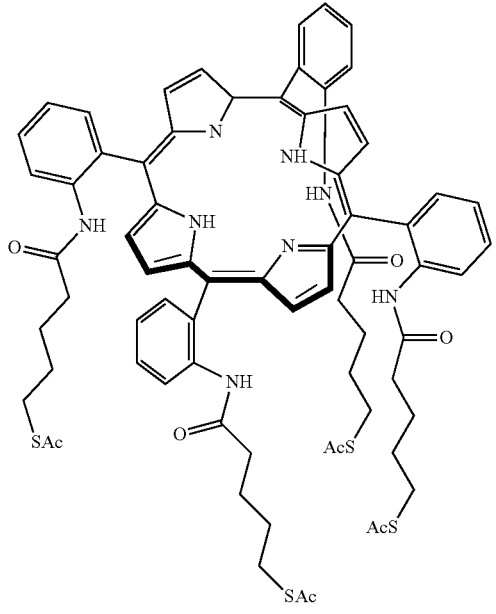

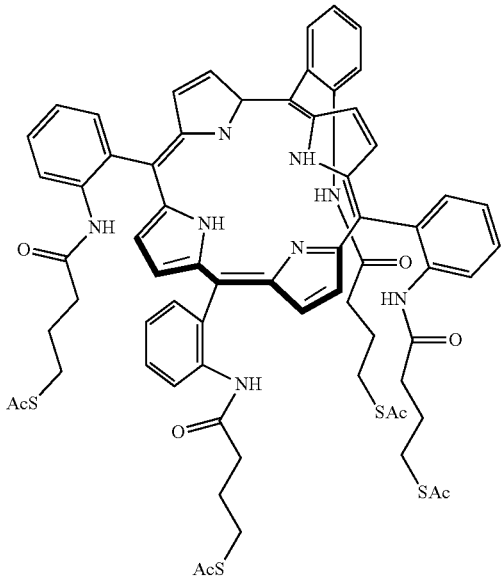

H₂PC₄SAc, Synthesized according to the general procedure. Purple solid; ¹H NMR (400 MHz, Chloroform-d) δ 8.88 (s, 8H), 8.71 (d, J=8.4 Hz, 4H), 7.92 (d, J=7.5 Hz, 4H), 7.90-7.84 (m, 4H), 7.52 (t, J=7.5 Hz, 4H), 7.15 (s, 4H), 2.17 (t, J=7.3 Hz, 8H), 2.04 (s, 12H), 1.44 (t, J=7.1 Hz, 8H), 1.21 (dd, J=10.2, 5.2 Hz, 8H), 1.00 (d, J=7.6 Hz, 8H); ¹³C NMR (101 MHz, CDCl₃) δ 195.46, 170.45, 138.23, 135.32, 131.83, 131.11, 130.02, 123.35, 121.93, 115.32, 36.15, 30.43, 28.45, 28.10, 23.82; MS (HR-ESI) m/z cal'd $C_{72}H_{75}N_8O_8S_4$ [M+H]⁺ 1307.4591, found 1307.4603. The structure of H₂PC₄SAc is:

4. Procedures for Electrode and Electrolyte Preparation

Cu functionalization: Cu foil was first sonicated in 0.5 M sulfuric acid (H₂SO₄) aqueous solution for 2 minutes and then sonicated in 0.1 M H₂SO₄ methanol solution for another 2 minutes. Then, the Cu foil was washed thoroughly with methanol and dried in inert atmosphere. After dried, the Cu foil was immersed in ~5 ml anhydrous N,N-dimethylformamide (DMF) containing 1 mg deprotected MPC$_n$SAc molecule and 0.3 mg sodium borohydride (NaBH₄) (The deprotection was performed by hydrolysis of MPC$_n$SAc in ammonia methanol/chloroform mixed solution (volume ratio=1/5) at room temperature). The porphyrin solution was constantly stirred under vacuum for 12 hours. After functionalization, the Cu foil was washed repetitively with dichloromethane to get rid of the unbound porphyrin molecules. The washed Cu foil was further heated in N₂ at 60° C. for 30 min to enhance the stability of the porphyrin molecule on the Cu surface. The Cu foil was ready for use after cooled to room temperature.

Electrodeposition of Cu: Glassy carbon (GC) rod was cleaned by sonication in water, acetone and methanol respectively. Electrodeposition of Cu was carried out in a two-electrode configuration under a constant current density of 10 mA/cm² for 30 min in an aqueous solution of 0.1 M sodium chloride (NaCl, >99.9%) with 10 mM copper sulfate (CuSO₄, from copper sulfate pentahydrate, 99.999% trace metals basis). The GC rod was used as working electrode and the graphite rod was used as counter electrode. After electrodeposition, the Cu-coated glassy carbon was immediately transferred to the porphyrin DMF solution in inert atmosphere for functionalization. The functionlization procedure was identical to that on Cu foil.

E-beam evaporation of 100 nm Cu on silicon wafer: A 4-inch Si wafer was coated first with 5 nm Cr layer, followed by 100 nm Cu with 0.4 Angstrom/sec deposition rate. The coating was performed at a high vacuum of ~5×10⁻⁷ torr. After e-beam evaporation, the wafer was immediately transferred to a N₂-filled glovebox for storage. The Cu-coated Si wafer was cut in the glovebox and then subject to the standard functionalization procedure.

Electrolyte preparation: The electrolyte was prepared using high-purity potassium hydroxide (>99.97% trace metals basis) and Milli-Q water with a concentration of 0.1 M. The electrolyte was further electrolyzed under a constant current of 0.25 mA using two graphite rod as electrodes in a two-electrode configuration for 12 hours to remove the residual metal impurities. After electrolysis, the electrolyte was filtered and stored for use.

5. Electrochemical Measurements

CO reduction measurements: All the electrochemical experiments were carried out in our customized two-compartment cell. The two compartments were separated by an anion exchange membrane (Selemion AMV). The cathodic and anodic compartment holds 130 ml and 50 ml electrolyte respectively. Graphite was used as the counter electrode and Ag/AgCl (3 M KCl) was used as reference electrode. Cu foil subjected to the identical porphyrin functionalization procedure with $NaBH_4$ treatment, but without porphyrin addition, was used as the working electrode for the control group. The potential scale was converted to the reversible hydrogen electrode (RHE) scale by E (V vs RHE)=E (V vs Ag/AgCl)+0.210 V+0.0591*pH. Prior to CO measurement, the electrolyte was saturated with CO for at least 30 minutes under stirring conditions. The CO pressure was then increased to 1.2 atm and the cell was sealed to maintain positive pressure of CO. Controlled potential electrolysis under different potentials was carried out for product analysis. All electrochemical measurements were iR-compensated.

Underpotential deposition: The underpotential deposition was carried out in a three electrode configuration according to previously reported conditions[6]. 0.01 M perchloric acid ($HClO_4$)+0.5 mM lead perchlorate ($Pb(ClO_4)_2$)+0.5 mM hydrochloric acid (HCl) was used as electrolyte, Ag/AgCl electrode was used as the reference electrode and ~1 $cm^2$ 100 nm Cu/Si wafer was used as working electrode. The two-compartment cell was used in order to prevent disturbance from the oxidized species generated on the counter electrode. The cell was purged with Ar for 30 minutes prior to the measurement to remove the residual $O_2$ in the electrolyte. The cyclic voltametry curves were taken at a scan rate of 10 mV/s.

Other electrochemical measurements: Acetaldehyde reduction was carried out in the same two-compartment cell under Ar atmosphere with 0.1 M KOH+10 mM or 50 mM acetaldehyde as electrolyte. For measurement on the activity of iron porphyrin alone, ~1 mg $FePC_2SAc$ dropdried onto a glassy carbon electrode was used as working electrode. Since the acetaldehyde can be quickly decomposed in alkaline electrolytes, the NMR analysis was performed immediately after the controlled potential electrolysis. Electrochemical impedance spectroscopy was measured in the frequency range of 1 Hz-1M Hz, and the final spectroscopy was fitted into the Nyquist plot.

6. Characterization Details

X-ray photoelectron spectroscopy (XPS): Survey XPS spectra were obtained with analyzer pass energy of 178.95 eV and step size of 1 eV. High resolution spectra were obtained with analyzer pass energy of 35.75 eV and 0.1 eV energy steps. The binding energy scale was corrected setting C 1 s peak in 284.6 eV.

External reflection Fourier transform infrared (FTIR) spectroscopy: The incident IR beam was reflected off the sample substrate at the incident angle of 60 degrees, and the spectra were acquired with a resolution of 1 $cm^{-1}$. Absorption due to air ($CO_2$ and water vapor) was subtracted off.

Density Functional Theory (DFT) calculations: The calculations in current study have been performed using the Vienna Ab-initio Simulation Pakage (VASP)[7,8] with plane wave basis set. We have used the projector-augmented-wave method (PAW)[9,10] in conjunction with Generalized Gradient Approximation (GGA) and Perdew-Burke-Ernzerh (PBE)[11] exchange correlation functional. The Brillouin zone was sampled using 8×8×8 and 1×1×1 (namely Gamma point) for bulk and surface calculations, respectively. A cutoff energy of 300 eV is employed for the plane-wave expansion. A total energy convergence better than $10^{-4}$ eV was reached and the interatomic forces are minimized up to 0.05 eV/Å for structural relaxation calculations.

In bulk calculations, both the cell dimensions and atomic positions were fully relaxed during the optimization. The calculated lattice constant of cubic Cu cell is 3.616 Å, which is consistent with 3.615 Å in experiment. The slab model was built by adding a vacuum region of 15 Å to prevent the slab from interacting with its periodic images in the surface normal direction. The adsorption calculations were calculated on a p(5×5) supercell of Cu(100) surface. As shown in FIGS. 13A-13C, the slab model with three atom layers contains 150 atoms, the two topmost layers were allowed to relax and the bottom one layer was fixed to its equilibrium position as in bulk. The adsorption energy per molecule was calculated from the relation $$E_{ads}=E_{surf+mol}-(E_{surf}+E_{mol})$$

where $E_{ads+mol}$ is the total energy of adsorbate-substrate system, $E_{surf}$ is the energy of pure slab model (Cu(100) and pre-adsorbed Cu(100) porphyrin) and $E_{mol}$ is the energy of the isolated molecular (C=C=O). So the negative adsorption energy indicates an exothermic process.

TABLE 2

Comparison of adsorption energy of ketene intermediates on Cu (100) and on Cu(100)—$H_2PC_1SH$

|  | Cu (100) | Cu(100)—$H_2PC_1SH$* |
|---|---|---|
| $E_{ads}$ (ketene) | −0.85 eV | −1.21 eV |

*Porphyrin with C1 linker was used as a model for calculation to demonstrate the concept. The distance and energy might change in the presence of electric field, but calculation involving electric field in the surface-tethered porphyrin systems takes a tremendous amount of time to finish.

NMR spectra of the porphyrins were determined.

REFERENCES CITED (1) Ohyama, J.; Hitomi, Y.; Higuchi, Y.; Tanaka, T. *Topics in Catalysis* 2009, 52, 852.
(2) Hitomi, Y.; Aoki, K.; Miyachi, R.; Ohyama, J.; Kodera, M.; Tanaka, T.; Sugihara, F. *Chemistry Letters* 2014, 43, 1901.
(3) Singhal, P.; Ghorpade, P. V.; Shankarling, G. S.; Singhal, N.; Jha, S. K.; Tripathi, R. M.; Ghosh, H. N. *Nanoscale* 2016, 8, 1823.
(4) Fulmer, G. R.; Miller, A. J.; Sherden, N. H.; Gottlieb, H. E.; Nudelman, A.; Stoltz, B. M.; Bercaw, J. E.; Goldberg, K. I. *Organometallics* 2010, 29, 2176.
(5) Adler, A. D.; Longo, F. R.; Kampas, F.; Kim, J. *Journal of Inorganic and Nuclear Chemistry* 1970, 32, 2443.
(6) Brisard, G. M.; Zenati, E.; Gasteiger, H. A.; Markovic, N.; Ross Jr, P. N. *Langmuir* 1995, 11, 2221.
(7) Kresse, G.; Furthmüller, J. *Computational Materials Science* 1996, 6, 15.
(8) Kresse, G.; Furthmüller, J. *Physical Review B* 1996, 54, 11169.

(9) Kresse, G.; Joubert, D. *Physical Review B* 1999, 59, 1758.
(10) Blöchl, P. E. *Physical Review B* 1994, 50, 17953.
(11) Perdew, J. P.; Burke, K.; Ernzerhof, M. *Physical Review Letters* 1996, 77, 3865.

What is claimed is:

1. A composition comprising a heterostructure capable of electrochemical CO reduction to a carbon-carbon product, wherein the heterostructure has the following structure:

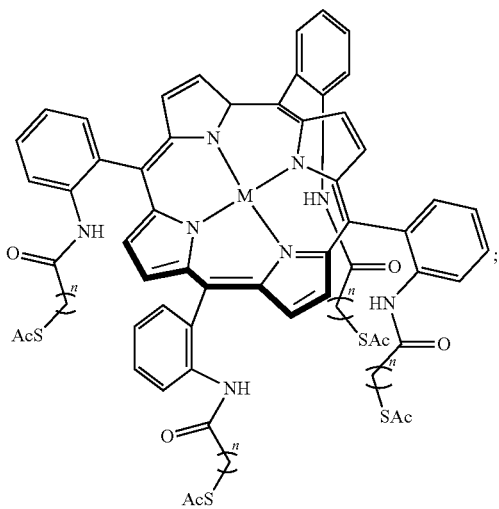

wherein (a) M is any metal, or halide of the metal thereof, and (b) n is any integer from 0 to 20.

2. The composition of claim 1, wherein M is any transition metal.

3. The composition of claim 1, wherein M is Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Rf, Db, Sg, Bh, or Hs, or a halide thereof.

4. The composition of claim 3, wherein the halide is a fluoride, bromide or chloride.

5. The composition of claim 1, wherein n is any integer from 0 to 10.

6. The composition of claim 1, wherein the heterostructure is capable of electrochemical CO reduction to a carbon-carbon product with one or more of the following properties: a Faradaic efficiency equal to or greater than 40%, a current density of equal to or greater than 0.5 mA/cm$^2$), and a potential of −0.40 V vs RHE.

7. The composition of claim 6, wherein the heterostructure is capable of electrochemical CO reduction to a carbon-carbon product with a Faradaic efficiency equal to or greater than 40%.

8. The composition of claim 6, wherein the heterostructure is capable of electrochemical CO reduction to a carbon-carbon product with a current density of equal to or greater than 1.34 mA/cm$^2$.

9. The composition of claim 3, wherein M is Fe.

10. The composition of claim 9, wherein n is 2.

11. The composition of claim 1, wherein n is 2.

12. The composition of claim 7, wherein the heterostructure is capable of electrochemical CO reduction to a carbon-carbon product with a Faradaic efficiency equal to or greater than 60%.

13. The composition of claim 12, wherein the heterostructure is capable of electrochemical CO reduction to a carbon-carbon product with a Faradaic efficiency equal to or greater than 80%.

* * * * *